(12) United States Patent
McKeown

(10) Patent No.: US 7,192,700 B2
(45) Date of Patent: Mar. 20, 2007

(54) METHODS AND COMPOSITIONS FOR CONDUCTING PRIMER EXTENSION AND POLYMORPHISM DETECTION REACTIONS

(75) Inventor: Brian McKeown, Oxford (GB)

(73) Assignee: Orchid Cellmark Inc., Princeton, NJ (US)

( * ) Notice: Subject to any disclaimer, the term of this patent is extended or adjusted under 35 U.S.C. 154(b) by 433 days.

(21) Appl. No.: 10/328,150

(22) Filed: Dec. 20, 2002

(65) Prior Publication Data

US 2004/0121342 A1  Jun. 24, 2004

(51) Int. Cl.
*C12Q 1/68* (2006.01)
*C12P 19/34* (2006.01)
*C07H 21/04* (2006.01)

(52) U.S. Cl. ............... 435/6; 435/91.2; 536/26.12; 536/23.1; 536/24.33; 536/26.1

(58) Field of Classification Search .......... 435/6, 435/91.2; 536/26.12, 23.1, 24.33, 26.1
See application file for complete search history.

(56) References Cited

U.S. PATENT DOCUMENTS

| | | | |
|---|---|---|---|
| 5,302,510 A | 4/1994 | Klevan | |
| 5,736,365 A | 4/1998 | Walker et al. | |
| 5,811,235 A | 9/1998 | Jeffreys | |
| 5,846,710 A | 12/1998 | Bajaj et al. | |
| 5,853,989 A | 12/1998 | Jeffreys et al. | |
| 5,856,092 A | 1/1999 | Dale et al. | |
| 5,858,732 A | 1/1999 | Solomon et al. | |
| 5,882,857 A | 3/1999 | Western et al. | |
| 5,888,819 A | 3/1999 | Goelet et al. | |
| 5,952,202 A | 9/1999 | Aoyagi et al. | |
| 5,962,221 A | 10/1999 | Caetano-Anolles | |
| 6,004,744 A | 12/1999 | Goelet et al. | |
| 6,013,431 A | 1/2000 | Soderlund et al. | |
| 6,027,889 A * | 2/2000 | Barany et al. ........... 435/6 |
| 6,074,831 A | 6/2000 | Yakhini et al. | |
| 6,090,590 A | 7/2000 | Kao | |
| 6,107,061 A | 8/2000 | Johnson | |
| 6,130,038 A | 10/2000 | Becker et al. | |
| 6,268,146 B1 | 7/2001 | Shultz et al. | |
| 6,268,147 B1 | 7/2001 | Beattie et al. | |
| 6,270,973 B1 | 8/2001 | Lewis et al. | |
| 6,287,778 B1 | 9/2001 | Huang et al. | |
| 6,294,336 B1 | 9/2001 | Boyce-Jacino et al. | |
| 6,537,748 B1 | 3/2003 | Goelet | |
| 2001/0009761 A1 | 7/2001 | Wright et al. | |
| 2003/0198977 A1 | 10/2003 | Nolan et al. | |
| 2004/0038256 A1 | 2/2004 | Van Ness et al. | |
| 2004/0166506 A1 | 8/2004 | McKeown et al. | |
| 2004/0185439 A1 | 9/2004 | Kalush et al. | |

FOREIGN PATENT DOCUMENTS

| | | |
|---|---|---|
| EP | 0416817 A2 | 3/1991 |
| EP | 0416817 A3 | 3/1991 |
| EP | 0416817 B1 | 3/1991 |
| EP | 0928832 A2 | 7/1999 |
| EP | 0332435 B2 | 10/1999 |
| GB | 2252407 A | 8/1992 |
| GB | 2252407 B | 8/1992 |
| GB | 2312747 A | 11/1997 |
| WO | WO 92/15712 | 9/1992 |
| WO | WO 93/25563 A1 | 12/1993 |
| WO | WO 97/42345 | 11/1997 |
| WO | WO 98/39475 | 9/1998 |

OTHER PUBLICATIONS

International Search Report PCT/US03/20150 dated Jun. 9, 2005.
Piggee, et al., "Capillary electrophoresis for the detection of known point mutations by single-nucleotide primer extension and laser-induced fluorescence detection"; Journal of Chromatography A. No. 781, pp. 367-375 (1997).
Mangano, et al., "Composition dependent separation of oligonucleotides by capillary electrophoresis in acidic buffers with application to the quality control of synthetic oligonucleotides", Journal of Chromatography A. No. 848, pp. 435-442 (1999).
Pastinen et al., Multiplex, fluorescent, solid-phase, minisequencing for efficient screening of DNA sequence variation. Clinical Chemistry, vol. 29, No. 9, pp. 1391-1397 (1996).
Accession No. M12480, (1994) Humanapolipoprotein B-100 nRNA.
Accession No. X53271, (1993) *H. sapiens* mRNA for ornithine decarboxylase.
Accession No. M86631, (2001) *Homo sapiens* (clone ST-18-5(9/16)) cystic fibrosis transmembrane conductance regulator (CFTR) gene, 3' end intron 17B; complete exon 18; complete intron 18.

* cited by examiner

*Primary Examiner*—Kenneth R. Horlick
*Assistant Examiner*—Joyce Tung
(74) *Attorney, Agent, or Firm*—William D. Schmidt; Kalow & Springut LLP

(57) ABSTRACT

The invention comprises compositions and methods for performing primer extension reactions, including employment of amplification primers having 5' tags to incorporate into amplicons variant nucleotides of interest from target nucleic acids at known ratios, along with the sequences surrounding the variant nucleotides of interest. The invention comprises identifying the variant nucleotides generated from the target nucleic acid and generated from the 5' tags, comparing the results, evaluating the efficiency of the primer extension reactions, and monitoring the efficacy of such reactions. The invention accounts for DNA sequence and experimental variables which may affect efficiency of incorporation of nucleotides, and provides a reference point for the interpretation of polymorphisms.

50 Claims, 20 Drawing Sheets

Figure 3
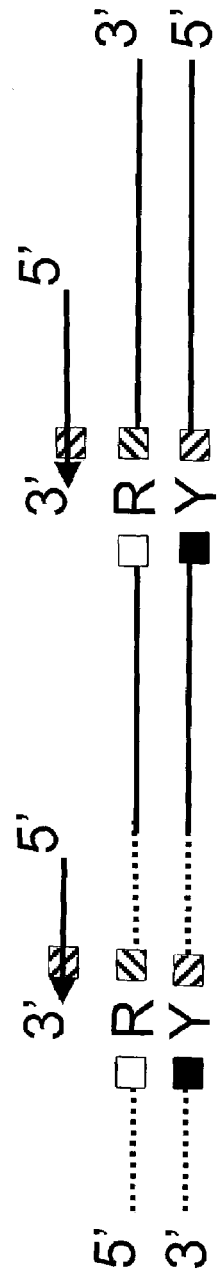
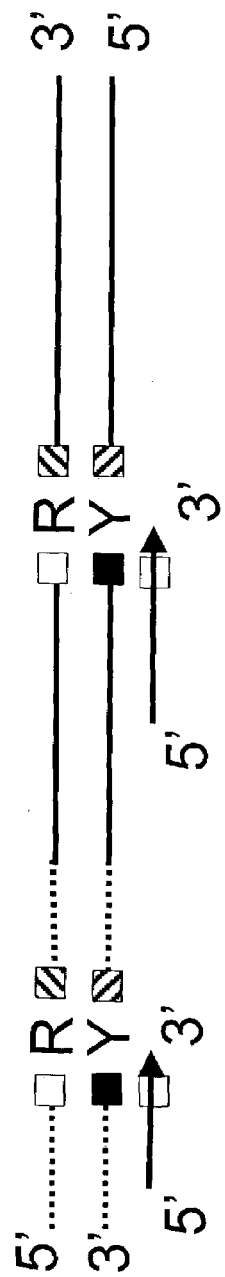
C/T SBE Reaction Primers
A/G SBE Reaction Primers

Figure 15
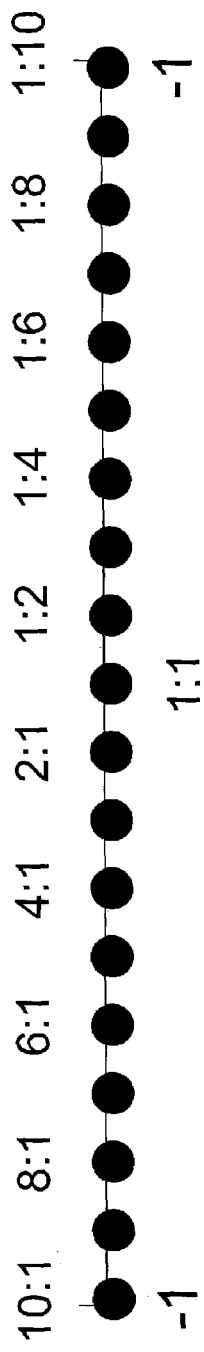
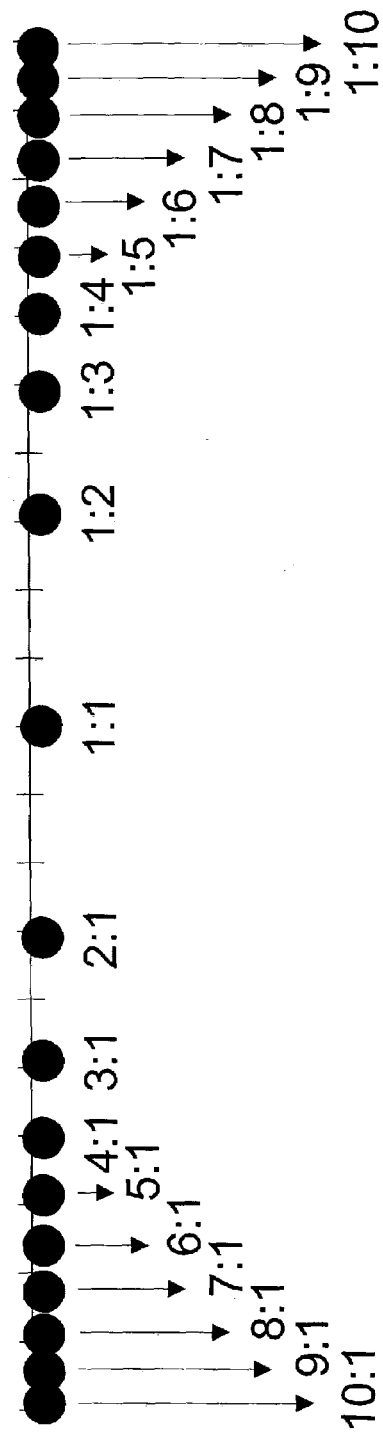

SEQUENCE LISTING

```
<160> NUMBER OF SEQ ID NOS: 28

<210> SEQ ID NO 1
<211> LENGTH: 879
<212> TYPE: DNA
<213> ORGANISM: Ovis aries

<400> SEQUENCE: 1
gttggctttc gtgtttgctg ctgtcctcat agatttcaca tggattagag gtcctccaaa       60
tggagtgctg cccaccttga ccactctttc ccatgcttct tgcctgctgc ttcacatggt      120
ccaggtggac tgcttttctc cccgcttaca tttcctagaa agtgccctgc tcacccttt       180 ctctggatgc tcactcaggg gttttaccag gcctgaactc tctccatgct gtgccgcttc      240
acccaactga ggccttctca ttcttcactt tgtagtcaag gaatctgcag cccagaagct      300
cctccatttt cctccagact agcccaggtc tcataccctt tggtttcacc tttctgtact      360
tctttcatgt tgcccaggat aattcctcat cattacttgt caaatggttg tgttctccct      420
gggctacaga ttagatgagg ttgggaattc ccttttcact gcctctgtat ctcaatagca      480
gccccatgcc aaacacttcc cagggactga gtaaagattt ccccaaaggg tgagtgaatg      540
ttgaggaaag gcagaaagca atcctcctta agtgggatat cagaatgctg agcttaactt      600
gaaaccgttt ctaaaccata gactcttatt taaaggaaac caacatgaaa atgccaacac      660
caccttattt acaaggtact ttgttcacta gagctattaa agggctgtgt tgatgggaag      720
ctgtgtataa ttgtaggtat tatgccagag accgctttct gtcaggctgc cagaccaaag      780
gggtagggac cgtactctag agaccctcac ccaacaggat gattaaacga atttgtaagg      840
gttaatagat gggcggtggc tcattaaaac caactctaa                              879

<210> SEQ ID NO 2
```

```
<210> SEQ ID NO 2
<211> LENGTH: 27
<212> TYPE: DNA
<213> ORGANISM: Ovis aries

<400> SEQUENCE: 2
ccctgctcac cctttttctct ggatgct                              27

<210> SEQ ID NO 3
<211> LENGTH: 25
<212> TYPE: DNA
<213> ORGANISM: Ovis aries

<400> SEQUENCE: 3
gagaaggcct cagttgggtg aagcg                                 25

<210> SEQ ID NO 4
<211> LENGTH: 45
<212> TYPE: DNA
<213> ORGANISM: Ovis aries

<400> SEQUENCE: 4
tcctcgatta cttgtcagcc ctgctcaccc ttttctctgg atgct           45

<210> SEQ ID NO 5
<211> LENGTH: 45
<212> TYPE: DNA
<213> ORGANISM: Ovis aries

<400> SEQUENCE: 5
tcctcgatta cctgtcagcc ctgctcaccc ttttctctgg atgct           45

<210> SEQ ID NO 6
<211> LENGTH: 27
<212> TYPE: DNA
<213> ORGANISM: Ovis aries

<400> SEQUENCE: 6
ggttttacca ggcctgaact ctctcca                               27

<210> SEQ ID NO 7
<211> LENGTH: 24
<212> TYPE: DNA
<213> ORGANISM: Ovis aries

<400> SEQUENCE: 7
agaaaagggt gagcagggct gaca                                  24

<210> SEQ ID NO 8
<211> LENGTH: 740
<212> TYPE: DNA
<213> ORGANISM: Ovis aries

<400> SEQUENCE: 8
ctgccaagtg tagagtcgtc agggagcagg ccaggctggg ggctccctct gccctgacc    60 cctggggag ctgctgggag agtcctggcc tctcctgcat gtgcgtggct tgcttttgg   120 ctggactaag gattgcagcc atatgaaatg ctcattgctg tcctcatccc cctcccattg  180
gctgtcctgg aastcagctc cttttctgcag ggcagccact gcacaccttt cttctgtgtc  240
ctttcaggat gtcctgtgca cacacaagta tatatatata cacatatgtg tacacacaca  300
tatataaatc ctaggattag aatctctggc tcaagggatt ttgtgtcctg tagatactgt  360
gttttcgttt ttctgacttt ttcctgcaca ctgtagacta caccgtgtgc taccctgcat  420
```

-continued

```
ttgcgattat cagggaacat gtcttggacg tcgtccacag cagcccctcc agacctgccc    480
attcctcctg ctcaggcatt ccatactgtg aatcacttgc ttaaccacac cttgactgat    540
ggggacactt acttcttttc actgtgtctt ataatgcagc cctggatatc cttacactta    600
tttccttggc tacttgtatg aggacctttg taggattaaa tttgataact agaattgtgg    660
atcaaaaggt ttgtgcattt tcactttgat aaggatgacc acacccctagg atggttggct    720 gggatccctt tctctaacat                                                 740
```

<210> SEQ ID NO 9
<211> LENGTH: 28
<212> TYPE: DNA
<213> ORGANISM: Ovis aries

<400> SEQUENCE: 9

```
ccatatgaaa tgctcattgc tgtcctca                                        28
```

<210> SEQ ID NO 10
<211> LENGTH: 28
<212> TYPE: DNA
<213> ORGANISM: Ovis aries

<400> SEQUENCE: 10

```
gacacagaag aaaggtgtgc agtggctg                                        28
```

<210> SEQ ID NO 11
<211> LENGTH: 66
<212> TYPE: DNA
<213> ORGANISM: Ovis aries

<400> SEQUENCE: 11

```
ccaaagatcc tctggagcta actcctatgg tctagttgcc atatgaaatg ctcattgctg    60
tcctca                                                                66
```

<210> SEQ ID NO 12
<211> LENGTH: 66
<212> TYPE: DNA
<213> ORGANISM: Ovis aries

<400> SEQUENCE: 12

```
ccaaagatcc tctggagcta actcctatgg tctacttgcc atatgaaatg ctcattgctg    60
tcctca                                                                66
```

<210> SEQ ID NO 13
<211> LENGTH: 69
<212> TYPE: DNA
<213> ORGANISM: Ovis aries

<400> SEQUENCE: 13

```
aaatcggttg gattcgcttg acggaagtat tgagagtcgt ggacacagaa gaaaggtgtg    60
cagtggctg                                                             69
```

<210> SEQ ID NO 14
<211> LENGTH: 69
<212> TYPE: DNA
<213> ORGANISM: Ovis aries

<400> SEQUENCE: 14

```
aaatcggttg gattcgcttg acggaagtat tgagactcgt ggacacagaa gaaaggtgtg    60
``` cagtggctg 69

<210> SEQ ID NO 15
<211> LENGTH: 30
<212> TYPE: DNA
<213> ORGANISM: Ovis aries

<400> SEQUENCE: 15
agatcctctg gagctaactc ctatggtcta 30

<210> SEQ ID NO 16
<211> LENGTH: 26
<212> TYPE: DNA
<213> ORGANISM: Ovis aries

<400> SEQUENCE: 16
acagcaatga gcatttcata tggcaa 26

<210> SEQ ID NO 17
<211> LENGTH: 25
<212> TYPE: DNA
<213> ORGANISM: Ovis aries

<400> SEQUENCE: 17
gcacaccttt cttctgtgtc cacga 25

<210> SEQ ID NO 18
<211> LENGTH: 26
<212> TYPE: DNA
<213> ORGANISM: Ovis aries

<400> SEQUENCE: 18
ggattcgctt gacggaagta ttgaga 26

<210> SEQ ID NO 19
<211> LENGTH: 22
<212> TYPE: DNA
<213> ORGANISM: Ovis aries

<400> SEQUENCE: 19
cctcccattg gctgtcctgg aa 22

<210> SEQ ID NO 20
<211> LENGTH: 23
<212> TYPE: DNA
<213> ORGANISM: Ovis aries

<400> SEQUENCE: 20
gctgccctgc agaaaggagc tga 23

<210> SEQ ID NO 21
<211> LENGTH: 75
<212> TYPE: DNA
<213> ORGANISM: Ovis aries

<400> SEQUENCE: 21
tgaggatcca ctggatagct gaagctctgg acacgatgac atcgtcaagg tggtagccac 60
agtcagtgga acaag 75

<210> SEQ ID NO 22
<211> LENGTH: 75
<212> TYPE: DNA
<213> ORGANISM: Ovis aries

```
<400> SEQUENCE: 22
tgaggatcca ctggatagct gaagctctgg acatgatggc atcgtcaagg tggtagccac      60
agtcagtgga acaag                                                      75

<210> SEQ ID NO 23
<211> LENGTH: 69
<212> TYPE: DNA
<213> ORGANISM: Ovis aries

<400> SEQUENCE: 23
atgcacgcat agctgatacg gtcacctgta acatccgaag gtggtggtgg tgactgtgtg      60
ttgcttgac                                                             69

<210> SEQ ID NO 24
<211> LENGTH: 69
<212> TYPE: DNA
<213> ORGANISM: Ovis aries

<400> SEQUENCE: 24
atgcacgcat agctgatacg gtcacctgta ccatctgaag gtggtggtgg tgactgtgtg      60
ttgcttgac                                                             69

<210> SEQ ID NO 25
<211> LENGTH: 26
<212> TYPE: DNA
<213> ORGANISM: Ovis aries

<400> SEQUENCE: 25
tgactgtggc taccaccttg acgatg                                          26

<210> SEQ ID NO 26
<211> LENGTH: 27
<212> TYPE: DNA
<213> ORGANISM: Ovis aries

<400> SEQUENCE: 26
tccactggat agctgaagct ctggaca                                         27

<210> SEQ ID NO 27
<211> LENGTH: 26
<212> TYPE: DNA
<213> ORGANISM: Ovis aries

<400> SEQUENCE: 27
aacacacagt caccaccacc accttc                                          26

<210> SEQ ID NO 28
<211> LENGTH: 27
<212> TYPE: DNA
<213> ORGANISM: Ovis aries

<400> SEQUENCE: 28
cacgcatagc tgatacggtc acctgta                                         27
```

METHODS AND COMPOSITIONS FOR CONDUCTING PRIMER EXTENSION AND POLYMORPHISM DETECTION REACTIONS

BACKGROUND OF THE INVENTION

Extensive progress in the field of biotechnology over the last two decades has given rise to new and promising routes to the identification and investigation of genomic characteristics in all species. Specifically, advances in nucleic acid synthesis and sequencing have led to the development of the science of genomics. High-throughput sequencing technologies have enabled significant milestones such as the mapping of various genomes, including the human genome. With the ability to rapidly sequence large amounts of DNA, large-scale analysis of genomic characteristics has become possible. Technologies are now evolving to identify and characterize features of genomes pertinent to individual or population-based variations in genotypes that may be used for applications such as identifying an individual's susceptibility to a given disease, identifying characteristics of interest in a gene or a genome, and identifying genetic characteristics that cause or promote disease states. Among the most promising of avenues for characterizing genomic variance in individuals and populations is the analysis and characterization of genetic polymorphisms.

Polymorphisms relate to variances in genomes among different species, for example, or among members of a species, among populations or sub-populations within a species, or among individuals in a species. Such variances are expressed as differences in nucleotide sequences at particular loci in the genomes in question. These differences include, for example, deletions, additions or insertions, rearrangements, or substitutions of nucleotides or groups of nucleotides in a genome.

One important type of polymorphism is a single nucleotide polymorphism (SNP). Single nucleotide polymorphisms occur with a frequency of about 1 in 300 to about 1 in 1,000 base pairs, where a single nucleotide base in the DNA sequence varies among individuals. SNPs may occur both inside and outside the coding regions of genes. It is believed that many diseases, including many cancers, hypertension, heart disease, and diabetes, for example, are the result of mutations borne as SNPs or collections of SNPs in subsets of the human population. Currently, one focus of genomics is the identification and characterization of SNPs and groups of SNPs and how they relate to phenotypic characteristics of medical and/or pharmacogenetic relevance, for example.

A variety of approaches to determining, or scoring, the large variety of polymorphisms in genomes have developed. Although these methods are applicable to many types of genomic polymorphisms, they are particularly amenable to determining, or scoring, SNPs.

One preferred method of polymorphism detection employs enzyme-assisted primer extension. SNP-IT™ (disclosed by Goelet, P. et al. WO092/15712, and U.S. Pat. Nos. 5,888,819 and 6,004,744, each herein incorporated by reference in its entirety) is a preferred method for determining the identity of a nucleotide at a predetermined polymorphic site in a target nucleic acid sequence. Thus, this method is uniquely suited for SNP scoring, although it also has general applicability for determination of a wide variety of polymorphisms. SNP-IT™ is a method of polymorphic site interrogation in which the nucleotide sequence information surrounding a polymorphic site in a target nucleic acid sequence is used to design a primer that is complementary to a region immediately adjacent to the target polynucleotide, but not including the variable nucleotide(s) in the polymorphic site of the target polynucleotide. The primer is extended by a single labeled terminator nucleotide, such as a dideoxynucleotide, using a polymerase, often in the presence of one or more chain terminating nucleoside triphosphate precursors (or suitable analogs). A detectable signal or moiety, covalently attached to the SNP-IT™ primer, is thereby produced.

In some embodiments of SNP-IT™, the oligonucleotide primer is bound to a solid support prior to the extension reaction. In other embodiments, the extension reaction is performed in solution and the extended product is subsequently bound to a solid support. In an alternate embodiment of SNP-IT™, the primer is detectably labeled and the extended terminator nucleotide is modified so as to enable the extended primer product to be bound to a solid support.

Ligase/polymerase mediated genetic bit analysis (U.S. Pat. Nos. 5,679,524, and 5,952,174, both herein incorporated by reference) is another example of a suitable polymerase-mediated primer extension method for determining the identity of a nucleotide at a polymorphic site. Ligase/polymerase SNP-IT™ utilizes two primers. Generally, one primer is detectably labeled, while the other is designed to be bound to a solid support. In alternate embodiments of ligase/polymerase SNP-IT™, the extended nucleotide is detectably labeled. The primers in ligase/polymerase SNP-IT™ are designed to hybridize to each side of a polymorphic site on the same strand, such that there is a gap comprising the polymorphic site. Only a successful extension reaction, followed by a successful ligation reaction, results in production of a detectable signal. This method offers the advantages of producing a signal with considerably lower background than is possible by methods employing only hybridization or primer extension alone.

An alternate method for determining the identity of a nucleotide at a predetermined polymorphic site in a target polynucleotide is described in Söderlund et al., U.S. Pat. No. 6,013,431 (the entire disclosure of which is herein incorporated by reference). In this alternate method, nucleotide sequence information surrounding a polymorphic site in a target nucleic acid sequence is used to design a primer that is complementary to a region flanking, but not including, the variable nucleotide(s) at the polymorphic site of the target. In some embodiments of this method, following isolation, the target polynucleotide may be amplified by any suitable means prior to hybridization to the interrogating primer. The primer is extended, using a polymerase, often in the presence of a mixture of at least one labeled deoxynucleotide and one or more chain terminating nucleoside triphosphate precursors (or suitable analogs). A detectable signal is produced upon incorporation of the labeled deoxynucleotide into the primer.

Due to the large size of many studies that use SNP information, SNP detection must be rapid, amenable to high-throughput and reliable. Reliably interpreting the results of an assay for polymorphism detection or identification using SNP-based applications is an important consideration, particularly when employing multiplex and high-throughput protocols. Accurate quantitation of primer extension products is one method of interpreting results.

Thus, there is a need in the art of polymorphism detection and identification in a system that provides for the confirmation of amplification, and that provides for accurate detection and identification of polymorphisms, and that can provide for abundance analysis of reaction products, either separately or simultaneously. There is also a need for an assay wherein control reactions that mirror the diagnostic assay are conducted under similar conditions, reducing the effect of factors influencing the efficiency of incorporation of one nucleotide over another on the interpretation of assay results, particularly in multiplex applications.

SUMMARY OF THE INVENTION

In one embodiment, the invention comprises a method of performing a primer extension reaction, comprising: obtaining an amplicon having a sequence generated from a target nucleic acid and a sequence generated from a first strand amplification primer, by amplifying a target nucleic acid having a variant nucleotide flanked by an invariant nucleotide, wherein a first strand amplification primer is employed that comprises a 5' tag substantially incapable of hybridizing to the target nucleic acid under amplification conditions, and wherein the 5' tag contains the variant nucleotide of the target nucleic acid, and employing a second strand amplification primer; employing the amplicon in a primer extension reaction wherein the identity of the variant nucleotide in the sequence generated from the target nucleic acid is determined by hybridizing a first identification primer immediately adjacent to the variant nucleotide in the sequence generated from the target nucleic acid; hybridizing a second identification primer immediately adjacent to the variant nucleotide in the sequence generated from the amplification primers; extending the first and the second identification primers in the presence of one or more nucleotides and a polymerizing agent; determining the identity of the variant nucleotide generated from the target nucleic acid; and comparing extension product of the first identification primer and extension product of the second identification primer, thereby monitoring the primer extension reaction.

In another embodiment, the invention comprises a method of performing a primer extension reaction, comprising: obtaining a sample comprising target nucleic acid from one or more individuals; obtaining an amplicon population having a sequence generated from the sample and a sequence generated from a tagged first strand amplification primer, by amplifying nucleic acids in the sample having a variant nucleotide that is a transversion flanked in the 5' direction by an invariant nucleotide and flanked in the 3' direction by an invariant nucleotide, wherein the tagged first strand primer is employed that comprises a 5' tag substantially incapable of hybridizing to target nucleic acids in the sample, and wherein the 5' tag contains the variant nucleotide with its flanking invariant nucleotides, and wherein a second strand amplification primer is employed; employing the amplicon population in a primer extension reaction wherein the identity of the variant nucleotide in the sequence generated from the sample is determined by hybridizing a first identification primer immediately adjacent to the variant nucleotide in the sequence generated from the sample; hybridizing a second identification primer immediately adjacent to the variant nucleotide in the sequence generated from the amplification primer; extending the first and the second identification primers in the presence of one or more nucleotides and a polymerizing agent; determining the identity of the variant nucleotide generated from the sample; and comparing extension product of the first identification primer and extension product of the second identification primer, thereby performing the primer extension reaction.

In another embodiment, the invention comprises a method of performing primer extension utilizing at least two amplification primers comprising: obtaining a target nucleic acid comprising a variant nucleotide flanked by an invariant nucleotide; hybridizing to the target nucleic acid a first amplification primer having a 5' tag comprising the variant nucleotide flanked by the invariant nucleotide, wherein the 5' tag is substantially unable to hybridize to the target nucleic acid, and a second amplification primer; and extending the amplification primers in the presence of at least one or more nucleotides and a polymerizing agent, thereby performing primer extension.

In another embodiment, the invention comprises a composition, comprising: a primer having a region capable of hybridizing to a target nucleic acid wherein the target nucleic acid comprises a variant nucleotide and an invariant nucleotide, and wherein the primer further comprises a 5' tag region having the variant nucleotide and the invariant nucleotide of the target nucleic acid, and wherein the 5' tag region is substantially incapable of hybridizing to the target nucleic acid under conditions suitable for amplification of the target nucleic acid.

In another embodiment, the invention comprises a method of monitoring the efficiency of incorporation of chain terminators into primers in a primer extension reaction, comprising: generating a population of amplicons from a mixed sample of target nucleic acid, wherein the population of amplicons comprises sequences at known ratios; performing primer extension reactions on the population of amplicons employing chain terminators and employing a population of primers specific for the sequences; detecting and measuring efficiency of incorporation of chain terminators into the population of primers at the known ratios, thereby monitoring the efficiency of incorporation of chain terminators into primers in a primer extension reaction.

In yet another embodiment, the invention comprises a method of performing a primer extension reaction, comprising: obtaining a sample comprising target nucleic acid from one or more individuals; obtaining an amplicon population having a sequence generated from the sample and a sequence generated from a tagged first strand amplification primer, by amplifying nucleic acids in the sample having a variant nucleotide, wherein the tagged first strand primer is employed that comprises a 5' tag substantially incapable of hybridizing to target nucleic acids in the sample, and wherein the 5' tag contains the variant nucleotide, and wherein a second strand amplification primer is employed; employing the amplicon population in a primer extension reaction wherein the identity of the variant nucleotide in the sequence generated from the sample is determined by hybridizing a first identification primer immediately adjacent to the variant nucleotide in the sequence generated from the sample; hybridizing a second identification primer immediately adjacent to the variant nucleotide in the sequence generated from the amplification primer; extending the first and the second identification primers in the presence of one or more nucleotides and a polymerizing agent; determining the identity of the variant nucleotide generated from the sample; and comparing extension product of the first identification primer and extension product of the second identification primer, thereby performing the primer extension reaction.

For a better understanding of the present invention together with other and further advantages and embodiments, reference is made to the following description taken in conjunction with the examples, the scope of which is set forth in the appended claims.

BRIEF DESCRIPTION OF THE FIGURES

Preferred embodiments of the invention have been chosen for purposes of illustration and description, but are not intended in any way to restrict the scope of the invention. The preferred embodiments of certain aspects of the invention are shown in the accompanying figures, wherein:

FIG. 3 illustrates the products of a 50:50 diagnostic amplification (the products which would result from the amplification of FIG. 2) and shows how the lower or upper strand may be employed in a diagnostic primer extension reaction.

FIG. 15 illustrates possible mathematical relationships between efficiency of incorporation of two chain terminating nucleotides.

DETAILED DESCRIPTION OF THE PREFERRED EMBODIMENTS

Figure 1:
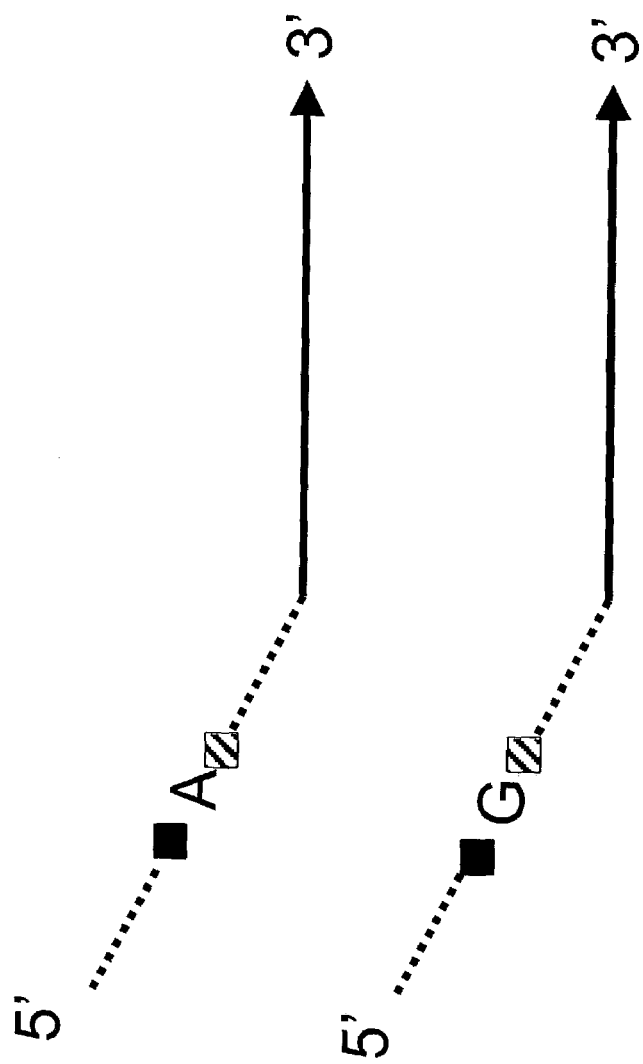
FIG. 1 illustrates two hybrid amplification primers, comprising a 3' end capable of hybridizing to some target DNA, and a 5' tag sequence substantially incapable of hybridizing to this target DNA.

The present invention provides methods and compositions for conducting primer extension reactions, nucleic acid amplification reactions and polymorphism identification reactions. Further, the present invention provides methods and compositions that monitor high throughput multiplex detection of polymorphisms.

DEFINITIONS

Flanking

The term flanking includes at least one or more unpaired nucleotide bases from the site of interest. Preferably, the one or more unpaired nucleotide bases are immediately adjacent to the site of interest. Most preferably, flanking means immediately adjacent to the site of interest. Thus, a variant nucleotide flanked on the 5' side by an invariant nucleotide describes a sequence wherein the invariant nucleotide is the very next nucleotide in the sequence in the 5' direction of the variant nucleotide. Similarly, a variant nucleotide flanked on the 3' side by an invariant nucleotide describes a sequence wherein the invariant nucleotide is the very next nucleotide in the sequence in the 3' direction of the variant nucleotide.

Variant Nucleotide

Variant nucleotides means nucleotides that are known to vary within or between individuals in a population at a given locus. Preferably, a population includes individuals of a given genus and species. The term variant nucleotide is meant to include a polymorphism in a nucleotide sequence. Polymorphic sites may display a great deal of variance in the population, or may vary in only one percent or less of the population. Polymorphisms may be either heterozygous or homozygous within an individual. Homozygous individuals have identical alleles at one or more corresponding loci on homologous chromosomes. Heterozygous individuals have different alleles at one or more corresponding loci on homologous chromosomes. As used herein, alleles include an alternative form of a gene or nucleic acid sequence, either inside or outside the coding region of a gene, including introns, exons, and untranscribed or untranslated regions. Alleles of a specific gene generally occupy the same location on homologous chromosomes. A polymorphism is thus said to be allelic, in that, due to the existence of the polymorphism, some members of a species carry a gene with one sequence (e.g., the original or wild-type allele), whereas other members may have an altered sequence (e.g., the variant or, mutant allele). In the simplest case, only one mutated variant of the sequence may exist, and the polymorphism is said to be biallelic. For example, if the two alleles at a locus are indistinguishable (for example A/A), then the individual is said to be homozygous at the locus under consideration. If the two alleles at a locus are distinguishable (for example A/G), then the individual is said to be heterozygous at the locus under consideration. The vast majority of known single nucleotide polymorphisms are bi-allelic—where there are two alternative bases at the particular locus under consideration. The term individual includes an individual of any species, including but not limited to humans. Variant nucleotides may arise in a variety of ways, and the term variant nucleotide is meant to include nucleotides that vary by reason of, for example, mutations, insertions, deletions, frameshifts, etc. Most preferably, the variant nucleotide is a single nucleotide polymorphism.

Invariant Nucleotide

Invariant nucleotides are nucleotides that do not vary among individuals of a given population at a given locus. Most preferably, the invariant nucleotide never varies between individuals of a population. Individuals of a population preferably are of the same genus and species, such as individual humans in a population of humans.

Tags

By the term 5' tag is meant a nucleotide sequence beginning at the 5' terminus of a primer and extending some distance in the 3' direction in the primer but is substantially incapable of hybridizing to the target nucleic acid. In the case of amplification primers, a 5' tag must be substantially unable to hybridize to the target nucleic acid under conditions sufficient to support amplification of sequences of the target nucleic acid. Tags can be non-complementary bases, or longer sequences that can be interspersed into the primer provided that the primer sequence has sufficient complementarity with the sequence of the target strand to hybridize therewith for the purposes employed. Preferably, the 5' tags bear little or no complementarity to the target nucleic acid. Most preferably, the 5' tags bear no complementarity to the target nucleic acid. However, apart from the 5' tags, the primers in the most preferred embodiment should have exact complementarity to invariant regions of the target nucleic acid(s) to which they hybridize to obtain optimal results. Thus, primers employed in the present invention may be substantially complementary in sequence and be able to form a double-stranded structure or hybrid with a target nucleotide sequence under the particular conditions employed. The exception to this general rule is the 5' tag region of amplification primers, which must be substantially unable to hybridize to the target nucleic acid under amplification conditions, and the 5' tag region of identification primers, which should also be substantially unable to hybridize to the amplicon or population of amplicons so as not to interfere with extension of the identification primers. Where invariant sequences in a target nucleic acid adjacent to a variant nucleotide are known, methods are available to those of ordinary skill in the art for selecting sequences that are substantially unable to hybridize to those sequences such that 5' tags can be designed that do not interfere with either the amplification or identification reactions. Preferably, the 5' tags should exhibit no more than about less than 1% to about 30% complementarity to the target nucleic acid. More preferably, the 5' tags should exhibit no more than about less than 1% to about 25% complementarity to the target nucleic acid. Most preferably, the 5' tags should exhibit no more than about less than 1% to about 5% complementarity to the target nucleic acid. Where 5' tags are designed to contain no invariant or variant nucleotides of the target nucleic acids, the 5' tags can exhibit no complementarity at all to the target nucleic acid.

Complementarity

A nucleic acid molecule is said to be the complement of another nucleic acid molecule—or itself—if it exhibits complete sequence complementarity. As used herein, molecules are said to exhibit complete complementarity when every nucleotide of one of the molecules is able to form a base pair with a nucleotide of the other. Substantially complementary refers to the ability of a nucleic acid molecule to hybridize to another nucleic acid molecule—or with itself—with sufficient stability to permit annealing under at least under at least conventional low-stringency conditions. Similarly, the molecules are said to be complementary if they can hybridize to one another with sufficient stability to permit them to remain annealed to one another under conventional high-stringency conditions. Conventional stringency conditions are described, for example, in Sambrook, J., et al., in Molecular Cloning, a Laboratory Manual, 2nd Edition, Cold Spring Harbor Press, Cold Spring Harbor, N.Y. (1989) (herein incorporated by reference). An explanation of the effect of ionic concentration and temperature on stringency can also be found in PCR Primer: A Laboratory Manual, Dieffenbach and Dveksler (Eds), Cold Spring Harbor Press, Cold Spring Harbor, N.Y. (1995) (herein incorporated by reference). Departures from complete complementarity are therefore permissible, as long as such departures do not preclude the capacity of the molecules to form a double-stranded structure or hybrid. Preferably, primers should exhibit, in the region not including the 5' tag, 80 to 100% complementarity to the target nucleic acid region they are designed to anneal with. More preferably, primers should exhibit, in the region not including the 5' tag, 90 to 100% complementarity to the target nucleic acid sequence they are designed to anneal with. Most preferably, primers should exhibit, in the region not including the 5' tag, 100% complementarity to the target to nucleic acid region they are designed to anneal with.

Primer Extension

Primer extension includes the extension of an oligonucleotide primer in a template-dependent manner, by one or more nucleotides. The one or more nucleotides can be one or more chain terminators, acylco terminators, non-chain terminating nucleotides and/or their analogs, and the like. Whatever the nucleotide or analog thereof is used, it need only be capable of being added to a primer in a template-dependent fashion by a polymerizing agent. Preferably, when amplification primers are extended, the nucleotides are all four deoxynucleotides dATP, dGTP, dTTP, and dCTP. Preferably, one or more labeled chain-terminators are employed where identification primers are extended. A preferred method of amplification is amplification employing thermally stable polymerizing agents, such as the polymerase chain reaction. Amplification conditions for employing thermally stable polymerases are well known in the art.

In a preferred embodiment, following amplification, the reaction mixture is preferably prepared prior to the use of identification primers. Many methods are known in the art to achieve this end, such as, for example, treating the reaction mixture with one or more phosphatases that will inactivate any deoxynucleotides present in the reaction mixture; adding one or more nucleases to remove single stranded primers, then separating or inactivating the phosphatases and nucleases prior to an identification step, and other measures known to those skilled in the art. Identification primers and a polymerizing agent are then added, preferably along with fluorescently labeled terminators, and primer extension is allowed to occur. Once the primer extension reaction has occurred, the products of the reaction are preferably analyzed using a capillary gel electrophoresis apparatus with a fluorescence detector. Such an apparatus separates the primers based on mass:charge ratio, and the identity of the detection primer can be ascertained by inspecting the distribution of the extended primers by fluorescence.

One preferred method of detecting polymorphic sites employs enzyme-assisted primer extension. SNP-IT™ (disclosed by Goelet, P. et al., and U.S. Pat. Nos. 5,888,819 and 6,004,744, each herein incorporated by reference in its entirety) is a preferred method for determining the identity of a nucleotide at a predetermined polymorphic site in a target nucleic acid sequence. Thus, it is uniquely suited for SNP scoring, although it also has general applicability for determination of a wide variety of polymorphisms. SNP-IT™ is a method of polymorphic site interrogation in which the nucleotide sequence information surrounding a polymorphic site in a target nucleic acid sequence is used to design an oligonucleotide primer that is complementary to a region immediately adjacent to, but not including, the variable nucleotide(s) in the polymorphic site of the target polynucleotide. The target polynucleotide is isolated from a biological sample and hybridized to the interrogating primer. Following isolation, the target polynucleotide may be amplified by any suitable means prior to hybridization to the interrogating primer. The primer is extended by a single labeled terminator nucleotide, such as a dideoxynucleotide, using a polymerase, often in the presence of one or more chain terminating nucleoside triphosphate precursors (or suitable analogs). A detectable signal is thereby produced.

Ligase/polymerase mediated genetic bit analysis (U.S. Pat. Nos. 5,679,524, and 5,952,174, both herein incorporated by reference) is another example of a suitable polymerase mediated primer extension method for determining the identity of a nucleotide at a polymorphic site. Ligase/polymerase SNP-IT™ utilizes two primers. Generally, one primer is detectably labeled, while the other is designed to be affixed to a solid support. In alternate embodiments of ligase/polymerase SNP-IT™, the extended nucleotide is detectably labeled. The primers in ligase/polymerase SNP-IT™ are designed to hybridize to each side of a polymorphic site, such that there is a gap comprising the polymorphic site. Only a successful extension reaction, followed by a successful ligation reaction, enables production of the detectable signal. The method offers the advantages of producing a signal with considerably lower background than is possible by methods employing either hybridization or primer extension alone.

An alternate method for determining the identity of a nucleotide at a polymorphic site in a target polynucleotide is described in Söderlund et al., U.S. Pat. No. 6,013,431 (the entire disclosure of which is herein incorporated by reference). In this method, the nucleotide sequence surrounding a polymorphic site in a target nucleic acid sequence is used to design an oligonucleotide primer that is complementary to a region flanking the 3' end, with respect to the polymorphic site, of the target polynucleotide, but not including the variable nucleotide(s) in the polymorphic site of the target polynucleotide. The target polynucleotide is isolated from the biological sample and hybridized with an interrogating primer. In some embodiments of this method, following isolation, the target polynucleotide may be amplified by any suitable means prior to hybridization with the interrogating primer. The primer is extended, using a polymerase, often in the presence of a mixture of at least one labeled deoxynucleotide and one or more chain terminating nucleoside triphosphate precursors (or suitable analogs). A detectable signal is produced on the primer upon incorporation of the labeled deoxynucleotide into the primer.

Once the primer extension reaction is employed, extended and unextended identification primers (if any) can be separated from each other so as to identify the polymorphic site on the one or more alleles that are interrogated. Separation of nucleic acids can be performed by any methods known in the art. Some separation methods include the detection of DNA duplexes with intercalating dyes such as, for example, ethidium bromide, hybridization methods to detect specific sequences and/or separate or capture oligonucleotide molecules whose structures are known or unknown and hybridization methods in connection with blotting methods well known in the art. Hybridization methods may be combined with other separation technologies well known in the art, such as separation of tagged oligonucleotides through solid phase capture, such as, for example, capture of hapten-linked oligonucleotides to immunoaffinity beads, which in turn may bear magnetic properties. Solid phase capture technologies also includes DNA affinity chromatography, wherein an oligonucleotide is captured by an immobilized oligonucleotide bearing a complementary sequence. Specific polynucleotide tags may be engineered into oligonucleotide primers, and separated by hybridization with immobilized complementary sequences. Such solid phase capture technologies also includes capture onto streptavidin-coated beads (magnetic or nonmagnetic) of biotinylated oligonucleotides. DNA may also be separated and with more traditional methods such as centrifugation, electrophoretic methods or precipitation or surface deposition methods. This is particularly so when the extended or unextended primers are in solution phase. The term solution phase is used herein to refer to a homogenous or heterogenous mixture. Such a mixture may be aqueous, organic, or contain both aqueous and organic components. As used herein, the term solution should be construed to be synonymous with suspension in that it should be construed to include particles suspended in a liquid medium.

In some embodiments of SNP-IT™, the primer is bound to a solid support prior to the extension reaction. In other embodiments, the extension reaction is performed in solution (such as in a test tube or a micro well) and the extended product is subsequently bound to a solid support. In an alternate embodiment of SNP-IT™, the primer is detectably labeled and the extended terminator nucleotide is modified so as to enable the extended primer product to be bound to a solid support. An example of this includes where the primer is fluorescently labeled and the terminator nucleotide is a biotin-labeled terminator nucleotide and the solid support is coated or derivatized with avidin or streptavidin. In such embodiments, an extended primer would thus be capable of binding to a solid support and non-extended primers would be unable to bind to the support, thereby producing a detectable signal dependent upon a successful extension reaction.

Preferably, the amplification reaction is multiplexed, where two or more or up to 100 or more polymorphic sequences are amplified simultaneously in the same reaction vessel. Preferably, the identification reaction is also multiplexed. Preferably, primer extension is carried out in the same reaction as the amplification reaction(s), and preferably sequentially. Amplification reactions carried out may require to be treated with such agents as Exonuclease I and Shrimp Alkaline Phosphatase, or other physical treatments such as size exclusion filtration, to remove certain components of the amplification reaction which may otherwise interfere with or prevent the primer extension reaction from proceeding.

Polymerizing Agent

Polymerizing agents are agents that are capable of extending a primer in a template-dependent manner. Polymerizing agents may be isolated or cloned from a variety of organisms including viruses, bacteria, archaebacteria, fungi, mycoplasma, prokaryotes, and eukaryotes. Preferred polymerizing agents include polymerases. More preferred are polymerases that tolerate and are active at temperatures greater than physiological temperatures, for example, at 50° C. to 70° C. or are tolerant of temperatures of at least 90° C. to about 95° C. Preferred polymerases include Taq™ polymerase from *T. aquaticus* (commercially available from ABI, Foster City, Calif.), Sequenase™ and ThermoSequenase™ (commercially available from U.S. Biochemical, Cleveland, Ohio), and Exo(−) polymerase (commercially available from New England Biolabs, Beverley, Mass.). Any polymerases exhibiting thermal stability may also be employed, such as for example, polymerases from *Thermus* species, including *Thermus aquaticus, Thermus brocianus, Thermus thermophilus, Thermus flavus, Thermococcus litoralis,* and *Thermogata maritime*; and polymerases from the *Pyrococcus* species, including *Pyrococcus furiosus, Pyrococcus* sp. GB-D, and *Pyrococcus woesei*. Biologically active proteolytic fragments, recombinant polymerases, genetically engineered polymerizing enzymes, and modified polymerases are included in the definition of polymerizing agent. It should be understood that the invention can employ various types of polymerases from various species and origins without undue experimentation.

Target Nucleic Acid

The present invention comprises obtaining a target nucleic acid sequence comprising a variant nucleotide and an invariant nucleotide. The target nucleic acid sequence will preferably be biologically active with regard to its capacity to hybridize with an oligonucleotide or a polynucleotide molecule. Target nucleic acid sequences may be either DNA or RNA, single-stranded or double-stranded or a DNA/RNA hybrid duplex. The target nucleic acid sequence may be a polynucleotide or oligonucleotide. Preferred target nucleic acid sequences are between 40 to about 2000 nucleotides in length, in order to facilitate detection. Exceptionally long segments of target nucleic acids, up to several tens of kb, may be required under some circumstances, such as, for example, when analyzing polymorphisms in regions of nucleic acids which have known pseudogenes, and long amplicons are required to enable the selection of amplification primers specific for the gene, rather than the pseudogene. Large target nucleic acid sequences may be cut or fragmented into shorter segments by methods known in the art e.g., by mechanical or hydrodynamic shearing methods such as sonication, or by enzymatic methods such as restriction enzymes or nucleases. These shorter segments may then be fractionated so that shorter sequences bearing the variant nucleotide(s) of interest are separated from any redundant sequences that might otherwise participate in undesirable side reactions during analysis of the variant nucleotides. Methods of recovering such fractionated DNA are well known in the art, and include, for example, gel electrophoresis, HPLC and techniques that employ hybridization to a capture sequence.

The target nucleic acid may be isolated, or derived from a biological sample. The term isolated as used herein refers to the state of being substantially free of other material such as non nuclear proteins, lipids, carbohydrates, or other materials such as cellular debris or growth media with which the target nucleic acid may be associated that can substantially interfere with the primer extension reactions described herein. The term isolated is not intended to refer to a complete absence of these materials. Neither is the term isolated generally intended to refer to the absence of stabilizing agents such as water, buffers, or salts, unless they are present in amounts that substantially interfere with the methods of the present invention. The term sample as used herein refers to any material that contains, or is suspected to contain, nucleic acid of interest, either DNA or RNA or DNA/RNA hybrids. Samples can be from any source including plants and animals including humans. Generally, such material will be in the form of a blood sample, a tissue sample, cells directly from individuals or propagated in culture, plants, yeast, fungi, mycoplasma, viruses, archaebacteria, histology sections, or buccal swabs, either fresh, fixed, frozen, or embedded in paraffin or another fixative, forensic samples, such as, for example, biological tissue, from a single individual or two or more individuals, alone or adhering to or mixed with non-biological material. One example of a suitable sample is venous blood taken into a collection device with an anticoagulant such as EDTA. Such a sample is amenable to template preparation by, for example, alkali lysis. Other sample types will be amenable to assay, but may require different or more extensive template preparation such as, for example, by phenol/chloroform extraction, or capture of the DNA onto a silica matrix in the presence of high salt concentration, or other methods. Many methods are known to those of ordinary skill in the art for retrieving or isolating nucleic acids from a wide variety of substances.

Preferably, the target nucleic acids are from or derived from genomic DNA drawn from one or more individuals, as, for example, in conducting a paternity test or a pharmacogenetic assay. Pharmacogenetic applications of the present invention may be employed, for example, to predict or determine a phenotypic characteristic associated with the identity of one or more variable nucleotides in a target nucleic acid or interest derived from an individual's genome. Such a phenotypic characteristic may be, for example, an individual's susceptibility to a particular disease state, an individual's prognosis with regard to one or more pathologies, an individual's likely response to a therapeutic regimen or agent, and the like. However, target nucleic acids need not necessarily be genomic DNA. Indeed, other forms of DNA, such as, for example, cDNA or cDNA libraries, can be employed in the invention. Indeed, virtually any nucleic acid having or suspected as having a variant nucleotide, and capable of being amplified in a primer extension reaction, should be suitable for use in the invention. In a preferred embodiment, the target nucleic acids are derived from a forensic sample.

The target nucleic acid may be, or may be derived from, either the upper or lower strand nucleic acids of double stranded DNA, RNA or other nucleic acid molecules. The upper strand of target nucleic acids includes the plus strand or sense strand of nucleic acids. The lower strand of target nucleic acids is intended to mean the minus or antisense strand that is complementary to the upper strand of target nucleic acids. Thus, reference may be made to either strand and still comprise the variant nucleic acid and a primer may be designed to hybridize to either or both strands. This is because variant nucleotides can be identified by identifying the variant nucleotide itself by, for example, employing amplification and identification primers aimed at elucidating the identity of a variant nucleotide in, for example, the coding strand of a gene, or employing amplification and identification primers aimed at elucidating the identity of a variant nucleotide in, for example, the corresponding non-coding strand of the gene. This is due to the complementarity of Watson-Crick base pairing. Thus, one of ordinary skill in the art will appreciate that the amplification and identification primers can be designed to reveal the identity of a variant nucleotide or its complement, and the tag or tags of the amplification primer(s) can be designed accordingly, as well as the identification primers.

Target nucleic acids are not meant to be limited to sequences within coding regions, but may also include any region of a genome, or portion of a genome, containing at least one variant nucleic acid. The term genome is meant to include complex genomes, such as those found in animals, not excluding humans, and plants, as well as much simpler and smaller sources of nucleic acids, such as nucleic acids of viruses, viroids, and any other biological material comprising nucleic acids. One example of a nucleic acid sequence suitable for analysis is an amplicon from within the coding sequence of the ovine PrP gene, which encodes the prion protein. The protein product of the PrP gene has known isoforms which can be assayed as the changes in PrP gene sequence. An amplicon comprising one or more variant nucleic acids is a suitable template for the invention described herein. Preferably, the target nucleic acid comprises a single nucleotide polymorphism.

The target nucleic acid sequences or fragment(s) thereof contain the variant nucleotide flanked by an invariant nucleotide, or include such nucleotides and sequences located either distal or proximal to the nucleotides. The variant nucleotides may be, or arise from, natural or induced mutations, deletions, insertions, re-arrangements, repetitive sequences, base modifications, or single or multiple base changes in a nucleic acid sequence. Such changes and the more prevalent, or normal, sequence may co-exist in a population. In some instances, these changes confer neither an advantage nor a disadvantage to the species or individuals within the species, and multiple alleles of the sequence may be in stable or quasi-stable equilibrium. In some instances, however, these sequence changes will confer a survival or evolutionary advantage to the species, and accordingly, an altered sequence or allele may eventually over time be incorporated into the genome of many or most members of that species. In other instances, the altered sequence or allele confers a disadvantage to the species, as where the mutation causes or predisposes an individual to a genetic disease or defect. As used herein, the terms mutation or polymorphic site refers to one or more variant nucleotides in a given sequence between some members of a species, a population within a species or between species. Such mutations or polymorphisms include, but are not limited to, single nucleotide polymorphisms (SNPs), one or more base deletions, or one or more base insertions.

Amplicon

An amplicon, as used herein, includes the product of a polymerase chain reaction wherein primers are employed in the presence of a template and one or more nucleotides and a template-dependent polymerizing agent to yield a nucleic acid. An amplicon product of a primer extension reaction is typically double-stranded. Where the amplicon is double stranded, the primers used to generate the amplicon are identical (that is, all upper strand primers are identical to each other and all lower strand primers are identical to each other), the sequences generated from the primers that wind up in the amplicon are identical in each amplicon molecule of the resulting amplicon population, except for the situation where the identical primers amplify a region of target DNA containing a variant nucleotide which is a heterozygote. Where the primers used to generate an amplicon are not identical (that is, not all upper strand primers are identical to one another, and/or not all lower strand primers are identical to one another), the amplicon is a population of molecules, or population of amplicons, where the sequences generated from the primers in the resulting amplicon are not identical, even in situations where the non-identical primers amplify a region of target DNA which does not contain any variant nucleotide. This situation arises when employing primers with different 5' tags. The present invention employs this phenomenon to advantage in conducting primer extension reactions. When the term amplicon is employed herein, it is meant to refer to a population of individual amplicon molecules. Such a population may contain amplicons that are identical, substantially identical, or that are not identical, as the case may be. Non-identical amplicon populations are generated through employment of non-identical primers, and/or the amplification of target DNA which contains a variant nucleotide.

The amplicon may have primer sequences introduced into it by, for example, employing a primer with a 5' tag. Such sequences can be introduced into an amplicon by employing them, for example, in the 5' end of the primer, referred to herein as a 5' tag. Such a 5' tag may comprise sequences that are natural or man-made. Either or both strands of an amplicon may have such sequences, depending on whether either or both upper and lower amplification primers bear such tags. Further, an amplicon may exist as a population of amplicons generated as the result of employing primers that differ in the characteristics of the 5' tag. Members of such a population of amplicons will comprise sequences generated as the result of employing the 5' tags and of sequences generated as the result of employing the target nucleic acid(s) as a template. In an amplicon, a sequence generated by an amplification primer refers to that portion of the amplicon that contains the primer sequence, including its 5' tag sequence. In an amplicon, a sequence generated by the target nucleic acid of the sample refers to that portion of the amplicon that contains the sequence of the target nucleic acid that has extended beyond the 3' terminus of the primers in a template-dependent manner, but will exclude the portion of the 3' extension which is complementary to the opposing primer. Typically, the sequence generated by the target nucleic acid can be located in an amplicon by noting the 3' terminus of the primer sequence in one strand, noting the 3' terminus of the primer sequence in the other strand, and observing that the intervening sequence corresponds to the sequence generated by the target nucleic acid. Preferably, double stranded amplicons are denatured prior to their use as templates in primer extension reactions.

Primers

One primer, or two or more primers, may be employed having 5' tags, or sequences, that are substantially incapable of hybridizing to the template, or target nucleic acid, as long as the primer includes sequences that allows for sufficient hybridization to the template, or target, so that desired sequences in the target nucleic acids can be amplified. This can be achieved by employing sequences that are substantially incapable of hybridizing to the template in, for example, the 5' end(s) of the primer(s). Substantially incapable of hybridizing to a target nucleic acid means unable to anneal or hybridize to the target nucleic acid and therefore cannot be extended in the primer extension reaction. Preferably, a 5' tag should exhibit less than 50% complementarity to target nucleic acid sequences in a sample or amplicon. More preferably, a tag should exhibit less than 10% or 20% complementarity to target nucleic acid sequences in a sample or amplicon. Most preferably, a 5' tag should exhibit the least amount of complementarity consistent with its use, which can be as low as 1% complementarity or less.

Primers can be polynucleotides or oligonucleotides capable of being extended in a primer extension reaction at their 3' end. In order for an oligonucleotide to serve as a primer, it typically need only be sufficiently complementary in sequence to be capable of forming a double-stranded structure with the template, or target, under the conditions employed. Establishing such conditions typically involves selection of solvent and salt concentration, incubation temperatures, incubation times, assay reagents and stabilization factors known to those in the art. The term primer or primer oligonucleotide refers to an oligonucleotide as defined herein, which is capable of acting as a point of initiation of synthesis when employed under conditions in which synthesis of a primer extension product that is complementary to a nucleic acid strand is induced, as, for example, in a DNA replication reaction such as a PCR reaction. Like non-primer oligonucleotides, primer oligonucleotides may be labeled according to any technique known in the art, such as with radioactive atoms, fluorescent labels, enzymatic labels, proteins, haptens, antibodies, sequence tags, and the like. Such labels may be employed by associating them, for example, with the 5' terminus of a primer by a plurality of techniques known in the art. Such labels may also act as capture moieties.

As used herein, the term polynucleotide includes nucleotide polymers of any number. The term oligonucleotide includes a polynucleotide molecule comprising any number of nucleotides, preferably, less than about 200 nucleotides. More preferably, oligonucleotides are between 5 and 100 nucleotides in length. Most preferably, oligonucleotides are 15 to 100 nucleotides in length. The exact length of a particular oligonucleotide or polynucleotide, however, will depend on many factors, which in turn depend on its ultimate function or use. Some factors affecting the length of an oligonucleotide are, for example, the sequence of the oligonucleotide, the assay conditions in terms of such variables as salt concentrations and temperatures used during the assay, and whether or not the oligonucleotide is modified at the 5' terminus to include additional bases for the purposes of modifying the mass:charge ratio of the oligonucleotide, and/or providing a tag capture sequence which may be used to geographically separate an oligonucleotide to a specific hybridization location on a DNA chip, for example.

Short primers may require lower temperatures to form sufficiently stable hybrid complexes with a template. The primers of the present invention should be complementary to the upper or lower strand target nucleic acids. Preferably, primers should not have self complementarity involving their 3' ends in order to avoid primer fold back leading to self-priming architectures and assay noise. Preferred primers of the present invention include oligonucleotides from about 8 to about 100 nucleotides in length, to longer polynucleotides that may be up to several thousand nucleotides long.

In practice, where sequences are introduced into an amplicon/amplicon population, amplification primers must be sufficiently long so as to, under a given set of conditions, (1) be able to hybridize with sufficient specificity to the target nucleic acid to generate the amplicon, and (2) have a 5' tag long enough to introduce a sequence into the resulting amplicon/amplicon population so that a primer extension reaction can be employed with an identification primer that can selectively anneal to the sequence which is at least partially the 5' tag region or is generated wholly by the 5' tag region. Any SNP introduced in the 5' tag can, just like any other SNP, be analyzed on either strand of the amplicon. If the SNP is introduced by the 'forward' primer, then it can either be analyzed by a primer designed to hybridize to the extended forward primer, or it can be designed to hybridize to the daughter strand of the forward primer. In the first instance, the SNP could be introduced very close to the portion of the initial amplification primer which is complementary to the target DNA, and the primer interrogating this SNP could be substantially complementary to the portion of the target specific sequence. This would minimize the size of the 5' tag, which is desirable from both a cost and efficiency of synthesis standpoint. In the second instance, the SNP could again be close to the junction of the non-hybridizable and the hybridizable portions of the initial amplification primer. In this case however, the interrogating primer would hybridize to the daughter strand, and would be at least very similar in sequence to the sequence of the non-hybridizable portion of the forward primer. In order to get good specificity, this second instance would require a substantial 5' tag sequence. See FIG. 16.

Primers of about 10 nucleotides are the shortest sequence that can be used to selectively hybridize to a complementary target nucleic acid sequence against the background of non-target nucleic acids in the present state of the art, although short sequences such as this will have greater potential to hybridize perfectly with multiple sites in a complex genome such as the greater than 3 billion base pair human genome. Therefore the size and complexity of total target DNA must be considered in order to design primers which will hybridize to just the target site intended. Most preferably, sequences of unbroken complementarity over at least 20 to about 35 nucleotides are used to assure a sufficient level of hybridization specificity, although length may vary considerably given the sequence of the target DNA molecule. The primers of this invention must be capable of specifically hybridizing, or annealing, to the target nucleic acid sequence—such as, for example, one or more upper primers hybridizing to one or more upper strand target nucleic acids or one or more lower strand nucleic acids. As used herein, two nucleic acid sequences are said to be capable of hybridizing to one another if the two molecules are capable of forming an anti-parallel, double-stranded nucleic acid structure or hybrid under conditions sufficient to promote such hybridization, whereas they must be substantially unable to form a double-stranded structure or hybrid with one another when incubated with a non-target nucleic acid sequence under the same conditions.

Detection

In yet another embodiment, the first and the second identification primers bear a detectable characteristic. The detectable characteristic may be the same or different on the first and second identification primers. The detectable characteristic may be a characteristic selected from the group consisting of mass, apparent mass, molecular weight, apparent molecular weight, a combination or ratio of mass and charge, number of bases, magnetic resonance, spectrophotometry, fluorometry, electric charge, polarimetry, light scattering, luminescence and antigen-antibody interaction. The identification primers can be modified by methods known by those of ordinary skill in the art to bear such characteristics. Preferably, the detectable characteristic comprises a capture tag. Primers tagged with capture tags can be applied to, for example, an array, an addressable array, or a virtual array, and the identity of the primer can be determined by its binding to such an array. Capture tags are meant to include nucleotide sequence tags, wherein capturing elements comprise the complements of the nucleotide sequence tags. Most preferably, the detectable characteristic is a change in mass: charge ratio induced by differential numbers of nucleotides in 5' tags, such that the primers are separable by capillary gel electrophoresis.

The primers of the present invention may be labeled at the 5' end. In a preferred embodiment, the identification primers are labeled at the 5' end. Labels include any label such as radioactive labels, fluorescent labels, enzymatic labels, proteins, haptens, antibodies, sequence tags, and the like. Preferably, the label does not interfere with the processes of the present invention. A preferred label includes a distinct nucleotide sequence that is complementary to a sequence bound to a solid support, where such solid support may include an array, including an addressable array or a virtual array. Thus, when the primer is exposed to the solid support under suitable hybridization conditions, the label hybridizes with the complementary sequence bound to the solid support. In this way, the identity of the primer can be determined by geometric location on the array, or by other means of identifying the point of association of the label with the capture moiety.

Most preferably, primer extension products of the identification primers are separated and identified by capillary gel electrophoreses wherein a fluorescence detector is employed to identify primer extension products labeled with fluorescent terminating nucleotides. In this most preferred embodiment, extended primers bearing fluorescent labels are separated by their mass:charge ratio. However, many separation and detection methods are known to those skilled in the art, and the invention herein is amenable to a wide variety of detection and separation protocols once this disclosure is in the hands of one skilled in the art. A primary advantage of the invention is the variety of detectable characteristics and tags that may be placed on the identification primers to aid in their separation and/or detection. Indeed, in the absence of tags, the primers of the invention may be separated, detected, and/or identified by their inherent physical characteristics or behavior, as is known to those skilled in the art.

The term detection refers to identification of a detectable moiety or moieties. The term is intended to include the ability to identify a moiety by electromagnetic characteristics, such as, for example, charge, light, fluorescence, chemiluminescence, changes in electromagnetic characteristics such as, for example, fluorescence polarization, light polarization, dichroism, light scattering, changes in refractive index, reflection, infrared, ultraviolet, and visible spectra, mass, mass:charge ratio and all manner of detection technologies dependent upon electromagnetic radiation or changes in electromagnetic radiation. The term is also intended to include identification of a moiety based on binding affinity, intrinsic mass, mass deposition, and electrostatic properties, size and sequence length. It should be noted that characteristics such as mass and molecular weight may be estimated by apparent mass or apparent molecular weight, so the terms mass or molecular weight as used herein do not exclude estimations as determined by a variety of instrumentation and methods, and thus do not restrict these terms to any single absolute value without reference to the method or instrumentation used to arrive at the mass or molecular weight.

Another method of detecting the nucleotide present at the polymorphic site is by comparison of the concentrations of free, unincorporated nucleotides remaining in the reaction mixture at any point after the primer extension reaction. Mass spectroscopy in general and, for example, electrospray mass spectroscopy, may be employed for the detection of unincorporated nucleotides in this embodiment. This detection method is possible because only the nucleotide(s) complementary to the polymorphic base is (are) depleted in the reaction mixture during the primer extension reaction. Thus, mass spectrometry may be employed to compare the relative intensities of the mass peaks for the nucleotides, Likewise, the concentrations of unlabeled primers may be determined and the information employed to arrive at the identity of the nucleotide present at the polymorphic site.

Support/Array

Preferred arrays for the present invention include, but are not limited to, addressable arrays including an array as defined above wherein individual positions have known coordinates such that a signal at a given position on an array may be identified as having a particular identifiable characteristic. Such arrays are commonly referred to as chips, biochips, biochip arrays, DNA chips, RNA chips, nucleotide chips, and oligonucleotide chips. Array, as used herein, is intended to include arrays in any shape or configuration, 2-dimensional arrays, and 3-dimensional arrays.

One particularly preferred array is the GenFlex™ Tag Array, from Affymetrix, Inc., that is comprised of capture probes for 2000 tag sequences. These are 20 mers selected from all possible 20 mers to have similar hybridization characteristics and at least minimal homology to sequences in the public databases.

Preferred separation methods employ exposing any extended and unextended primers to a solid support. Solid supports include arrays. The term array is used herein to refer to an ordered arrangement of immobilized biological molecules at a plurality of positions on a solid, semi-solid, gel or polymer phase. This definition includes phases treated or coated with silica, silane, silicon, silicates and derivatives thereof, plastics and derivatives thereof such as, for example, polystyrene, nylon and, in particular, polystyrene plates, glasses and derivatives thereof, including derivatized glass, glass beads, controlled pore glass (CPG). Immobilized biological molecules includes oligonucleotides that may include other moieties, such as tags and/or affinity moieties. The term array is intended to include and be synonymous with the terms chip, biochip, biochip array, DNA chip, RNA chip, nucleotide chip, and oligonucleotide chip. All these terms are intended to include arrays of arrays, and are intended to include arrays of biological polymers such as, for example, oligonucleotides and DNA molecules whose sequences are known or whose sequences are not known.

Transversion

By the term transversion is meant a variant nucleotide in a nucleotide sequence, wherein the variance is the occurrence of a purine in the place of a pyrimidine, or a pyrimidine in the place of a purine. It will be appreciated by one of skill in the art that normal transitions can also be used in these assays, although they will not regenerate the SNP in opposite ratio on the other strand, and so are not preferred for forensic applications. However, diagnostic, single template source applications only require that we know what a 1:1 heterozygote looks like upon performing the primer extension reaction.

Nucleotide

The primer extension reaction of the present invention employs a mixture of one or more nucleotides, labeled or not, and a polymerizing agent. The term nucleotide or nucleic acid as used herein is intended to refer to ribonucleotides, deoxyribonucleotides, acyclic derivatives of nucleotides, and functional equivalents or derivatives thereof, of any phosphorylation state capable of being added to a primer by a polymerizing agent. Functional equivalents of nucleotides are those that act as substrates for a polymerase as, for example, in an amplification method or a primer extension method. Functional equivalents of nucleotides are also those that may be formed into a polynucleotide that retains the ability to hybridize in a sequence-specific manner to a target polynucleotide. Examples of nucleotides include chain-terminating nucleotides, most preferably dideoxynucleoside triphosphates (ddNTPs), such as ddATP, ddCTP, ddGTP, and ddTTP; however other terminators known to those skilled in the art, such as, for example, acyclo nucleotide analogs, other acyclo analogs, and arabinoside triphosphates, are also within the scope of the present invention. Preferred ddNTPs differ from conventional 2'deoxynucleoside triphosphates (dNTPs) in that they lack a hydroxyl group at the 3'position of the sugar component.

The nucleotides employed may bear a detectable characteristic. As used herein a detectable characteristic includes any identifiable characteristic that enables distinction between nucleotides. It is important that the detectable characteristic does not interfere with any of the methods of the present invention. Detectable characteristic refers to an atom or molecule or portion of a molecule that is capable of being detected employing an appropriate method of detection. Detectable characteristics include inherent mass, electric charge, electron spin, mass tag, radioactive isotope, dye, bioluminescence, chemiluminescence, nucleic acid characteristics, haptens, proteins, light scattering/phase shifting characteristics, or fluorescent characteristics. As used herein, the phrase "same detectable characteristic" includes nucleotides that are detectable because they have the same signal. The same detectable characteristic includes embodiments where nucleotides are labeled with the same type of labels, for example, A and C nucleotide may be labeled with the same type of dye, where they emit the same type of signal.

Nucleotides and primers may be labeled according to any technique known in the art. Preferred labels include radiolabels, fluorescent labels, enzymatic labels, proteins, haptens, antibodies, sequence tags, mass tags, fluorescent tags and the like. Preferred dye type labels include, but are not limited to, TAMRA (carboxy-tetramethylrhodamine), ROX (carboxy-X-rhodamine), FAM (5-carboxyfluorescein), and the like.

The primer extension reactions of the present invention can employ one or more labeled nucleotide bases. Preferably, two or more nucleotides of different bases are employed in the identification step. Most preferably, the identification reaction of the present invention employs four nucleotides of different bases. In the most preferred embodiment all four different types of nucleotide are labeled with distinguishable labels. For example, A labeled with dR6G, C labeled with dTAMRA, G labeled with dR110 and T labeled with dROX.

Nucleotides may also be detected by, or labeled with moieties that can be detected by, a variety of spectroscopic methods relating to the behavior of electromagnetic radiation. These spectroscopic methods include, for example, electron spin resonance, optical activity or rotation spectroscopy such as circular dichroism spectroscopy, fluorescence, fluorescence polarization, absorption/emission spectroscopy, ultraviolet, infrared, visible or mass spectroscopy, Raman spectroscopy and nuclear magnetic resonance spectroscopy.

Nucleotides and analogs thereof, terminators and/or primers may be labeled according to any technique known in the art. Preferred labels include radiolabels, fluorescent labels, enzymatic labels, proteins, haptens, antibodies, sequence tags, mass tags, fluorescent tags and the like. Preferred dye type labels include, but are not limited to, TAMRA (carboxy-tetramethylrhodamine), ROX (carboxy-X-rhodamine), FAM (5-carboxyfluorescein), and the like.

In a preferred embodiment of the present invention, the target nucleic acid sequences are arranged in a format that allows multiple simultaneous detections (multiplexing), as well as parallel processing using oligonucleotide arrays.

Preferred applications of the specialized primers and methods taught herein include diagnostic polymorphism genotyping from a single source template, that is, from non-mixed sources. The primers and methods taught herein are applicable, for example, to any single nucleotide polymorphism in any sequence context. In such an embodiment, most preferably a control 1:1 heterozygotic site is introduced into the amplicon employing the primers described herein. In this embodiment, assay of the control heterozygotic site confirms amplicon generation and serves as a benchmark for analysis of the polymorphism of the target nucleic acid being investigated.

Preferred applications of the specialized primers and methods taught herein also include forensic single nucleotide polymorphism genotyping from mixed template sources. In such an embodiment, single nucleotide polymorphisms that are transversions are most preferred, wherein the nucleotide directly upstream of the transversion is complementary to the nucleotide directly downstream of the transversion. In such an embodiment, at least two inventive primers are employed. The first primer of this embodiment has a ratio of variant nucleotide X/Y of X:Y=3:1, which reverses on the daughter strand to X:Y=1:3. The second primer of this embodiment has a balanced ratio of variant nucleotide X/Y of X:Y=1:1, generating a heterozygous site.

One embodiment of the invention comprises a method of performing a primer extension reaction, comprising: obtaining an amplicon having a sequence generated from a target nucleic acid and a sequence generated from a first strand amplification primer, by amplifying a target nucleic acid having a variant nucleotide flanked by an invariant nucleotide, wherein a first strand amplification primer is employed that comprises a 5' tag substantially incapable of hybridizing to the target nucleic acid under amplification conditions, and wherein the 5' tag contains the variant nucleotide of the target nucleic acid, and employing a second strand amplification primer; employing the amplicon in a primer extension reaction wherein the identity of the variant nucleotide in the sequence generated from the target nucleic acid is determined by hybridizing a first identification primer immediately adjacent to the variant nucleotide in the sequence generated from the target nucleic acid; hybridizing a second identification primer immediately adjacent to the variant nucleotide in the sequence generated from the amplification primers; extending the first and the second identification primers in the presence of one or more nucleotides and a polymerizing agent; determining the identity of the variant nucleotide generated from the target nucleic acid; and comparing extension product of the first identification primer and extension product of the second identification primer, thereby performing the primer extension reaction.

In another embodiment of the invention, immediately adjacent in the 5' direction to the variant nucleotide in the 5'tag is the invariant nucleotide to the 5' direction of the variant nucleotide of the target nucleic acid. By immediately adjacent in the 5' direction is meant the next nucleotide in the 5' direction from the variant nucleotide. Thus, in this embodiment, the 5' tag comprises the variant nucleotide of the target nucleic acid and the next nucleotide in the 5' direction of the variant nucleotide, arranged as in the target nucleic acid.

In yet another embodiment of the invention, immediately adjacent in the 3' direction to the variant nucleotide in the 5' tag is the invariant nucleotide to the 3' direction of the variant nucleotide of the target nucleic acid. By immediately adjacent in the 3' direction is meant the next nucleotide in the 3' direction from the variant nucleotide in the target nucleic acid. Thus, the 5' tag can comprise the variant nucleotide of the target nucleic acid and the next nucleotide in the 3' direction of the variant nucleotide, arranged as in the target nucleic acid. In another embodiment of the invention, immediately adjacent in the 3' direction to the variant nucleotide in the 5' tag is the invariant nucleotide to the 3' direction of the variant nucleotide of the target nucleic acid, and immediately adjacent in the 5' direction to the variant nucleotide in the 5' tag is the invariant nucleotide to the 5' direction of the variant nucleotide of the target nucleic acid. Thus, the 5' tag can comprise the variant nucleotide of the target nucleic acid and both the next nucleotide in the 3' direction of the variant nucleotide and the next nucleotide in the 5' direction of the variant nucleotide, arranged as in the target nucleic acid. Further, the 5' tag can comprise at least two invariant nucleotides immediately adjacent in the 3' direction to the variant nucleotide, and at least two invariant nucleotides immediately adjacent in the 5' direction to the variant nucleotide, and wherein the at least two invariant nucleotides immediately adjacent in the 3' direction and the at least two invariant nucleotides immediately adjacent in the 5' direction are selected so as to be substantially homologous to the corresponding nucleotides flanking the variant nucleotide in the target nucleic acid. By substantially homologous to the corresponding nucleotides flanking the variant nucleotide in the target nucleic acid is meant that the flanking nucleotides in the 5' tag should be selected so as to present the same or similar sequence context as is present around the variant nucleotide in the target nucleic acid, with respect to the effect these flanking nucleotides would have on the incorporation of the variant nucleotide in a primer extension reaction.

In another embodiment of the invention, the identification primers are extended by one or more labeled nucleotide bases, and are capable of being detected by a characteristic selected from the group consisting of mass, apparent mass, molecular weight, apparent molecular weight, a combination or ratio of mass and charge, number of bases, magnetic resonance, spectrophotometry, fluorometry, electric charge, polarimetry, light scattering, luminescence and antigen-antibody interaction.

In another embodiment of the invention, the identification primers are extended by a chain terminator. Chain terminators may be dideoxynucleotides, acyclo terminators, and the like. The chain terminators may be labeled such that the resulting extended primers are detectable by characteristics such as mass, apparent mass, molecular weight, apparent molecular weight, a combination or ratio of mass and charge, number of bases, magnetic resonance, spectrophotometry, fluorometry, electric charge, polarimetry, light scattering, luminescence and antigen-antibody interaction. Preferably, the chain terminators are labeled with fluorescent or fluorogenic moieties, allowing their detection with, for example, conventional fluorescence detection instrumentation coupled to capillary electrophoresis apparatuses.

In another embodiment, identification primers are applied to virtual arrays where extended and unextended primers are separated on an array where the array comprises a suspension of microspheres, where the microspheres bear one or more capture moieties to separate the tagged primers. The microspheres, in turn, bear unique identifying characteristics such that they are capable of being separated on the basis of that characteristic, such as for example, diameter, density, size, color, and the like.

Another preferred array is the addressable array that has sequence tags that complement sequences 5' tags. These complementary tags are bound to the array at known positions. This type of tag hybridizes with the array under suitable hybridization conditions. By locating the bound primer in conjunction with detecting one or more extended primers, the nucleotide identity at the polymorphic site can be determined.

In another embodiment, the invention comprises varying the identity of the variant nucleotide in the 5' tag so as to generate a population of amplicons in which the identity of the variant nucleotide derived from the 5' tags is fixed at a known ratio. By varying the identity of the variant nucleotide in the 5' tag is meant employing primers where the identity of the nucleotide at the position of the variant nucleotide is not the same in all primer molecules. Thus, all primers may bear the invariant nucleotide flanked by either the variant nucleotide or another nucleotide that is not the invariant nucleotide. For example, where the variant nucleotide is a G/C SNP, then a primer population may be used that bears a G at the variant nucleotide site in one-half of the primer molecules, whereas the remaining half of the primer molecules bear a C at the variant nucleotide site. Amplification employing a target nucleic acid having such a G/C SNP will generate a population of amplicons wherein all will have the naturally occurring G/C SNP, but one-half will bear a G at the variant nucleotide site generated by the 5' tag sequence and the remaining half will bear a C at the variant nucleotide site generated by the 5' tag sequence. This population of amplicons can then be probed with identification primers that are specific for the variant site generated from the 5' tags and that are specific for the naturally occurring variant site. Thus, the variant nucleotide can be reproduced in the amplicon at a known ratio. In a preferred embodiment of the invention, the identity of the variant nucleotide in the 5' tag is varied so as to generate a population of amplicons that is a balanced heterozygous population with respect to the variant nucleotide. A balanced heterozygote is a mixture of DNA species in which there are equivalent concentrations of two distinct DNA sequences. In terms of the present invention, the use of equivalent concentrations of the 5' tag primers bearing equivalent concentrations of the variant nucleotides will result in an amplicon population in which there are two species with respect to the sequences derived from the 5' tag portions of the amplification primers. Such equivalence of distinct DNA sequences may be said to represent a balanced heterozygote.

In a preferred embodiment of the invention, the target nucleic acid comprises nucleic acids from two or more individuals. By two or more individuals is meant two or more biological entities that comprise nucleic acids. For example, the target nucleic acid may be a forensic sample, comprising nucleic acids from the victim of a crime and nucleic acids from one or more other individuals. The term individual is meant to include members of any species that harbors nucleic acids, and is not meant to be limited only to humans. Indeed, the sample may comprise nucleic acids from two or more different species or two or more individuals of different genus.

In another embodiment of the invention, two or more variant nucleotides are identified. The variant nucleotides may be on the same nucleic acid molecule, or target nucleic acid, or may be on separate nucleic acid molecules, or target nucleic acids. Preferably, the two or more variant nucleotides are on the same target nucleic acid molecule. Most preferably, the two or more variant nucleic acids are situated such that the invention can be practiced wherein they appear on the same amplicon molecule.

In another embodiment, the invention comprises a method of performing a primer extension reaction, comprising: obtaining a sample comprising target nucleic acid from one or more individuals; obtaining an amplicon population having a sequence generated from the sample and a sequence generated from a tagged first strand amplification primer, by amplifying nucleic acids in the sample having a variant nucleotide that is a transversion flanked in the 5' direction by an invariant nucleotide and flanked in the 3' direction by an invariant nucleotide, wherein the tagged first strand primer is employed that comprises a 5' tag substantially incapable of hybridizing to target nucleic acids in the sample, and wherein the 5' tag contains the variant nucleotide with its flanking invariant nucleotides, and wherein a second strand amplification primer is employed; employing the amplicon population in a primer extension reaction wherein the identity of the variant nucleotide in the sequence generated from the sample is determined by hybridizing a first identification primer immediately adjacent to the variant nucleotide in the sequence generated from the sample; hybridizing a second identification primer immediately adjacent to the variant nucleotide in the sequence generated from the amplification primer; extending the first and the second identification primers in the presence of one or more nucleotides and a polymerizing agent; determining the identity of the variant nucleotide generated from the sample; and comparing extension product of the first identification primer and extension product of the second identification primer, thereby performing the primer extension reaction.

In another embodiment of the invention, wherein the flanking invariant nucleotide in the 5' direction of the transversion is complementary to the flanking invariant nucleotide in the 3' direction of the transversion.

In another embodiment, the first strand amplification primer comprises the two or more nucleotides in the 5' direction immediately adjacent to the variant nucleotide of the first strand amplification primer, wherein the two or more nucleotides are identical to the two or more nucleotides immediately adjacent in the 5' direction of the variant nucleotide in the target. Thus, an identification primer employed to determine the variant nucleotide in the sequence generated by the 5' tag will employ the same two 3' terminal nucleotides as are present in the identification primer. In another embodiment of the invention, the first strand amplification primer comprises the two or more nucleotides in the 3' direction immediately adjacent to the variant nucleotide of the first strand amplification primer, wherein the two or more nucleotides are identical to the two or more nucleotides immediately adjacent in the 3' direction of the variant nucleotide in the target nucleic acid. In another embodiment of the invention, the first strand amplification primer comprises the two or more nucleotides in the 5' direction immediately adjacent to the variant nucleotide of the first strand amplification primer, and the two or more nucleotides in the 3' direction immediately adjacent to the variant nucleotide of the first strand amplification primer, each arranged as to be identical to the corresponding nucleotides flanking the variant nucleotide in the target nucleic acid. Inclusion of these invariant nucleotides around the variant nucleotide in the 5' tag will generate an amplicon, or population of amplicons, having a similar sequence context in the vicinity of the variant nucleic acid present in the target DNA, thus reducing DNA sequence context-sensitive effects that might otherwise confound results on primer extension with identification primers.

In another embodiment of the invention, the second strand amplification primer comprises a 5' tag having the variant nucleotide. The second strand amplification primer can also have the variant nucleotide, which can also be flanked, in either the 5' direction or the 3' direction or both, by the invariant nucleotide(s) flanking the variant nucleotide in the target. In the event that the variant nucleotide is a transversion, the first variant nucleotide in the 5' direction is complementary to the first variant nucleotide in the 3' direction flanking the transversion, and it is most preferred that both variant nucleotides be included in the 5' tag of the first strand amplification primer and in the 5' tag of the second strand amplification primer.

In another embodiment of the invention, the identity of the variant nucleotide in the first and second strand amplification primers is varied so as to generate a population of amplicons wherein the identity of the variant nucleotide is varied at a known ratio. Preferably, the identity of the variant nucleotide in the 5' tag of the first and second strand amplification primers is varied so as to generate an amplicon population comprising a ratio of one to one (1:1) and a ratio of three to one (3:1) with respect to the identity of the nucleotides in the amplicon population generated by the 5' tags. The resulting amplicon will, for example, have a ratio of 3:1 and 1:1 in the upper strand sequence generated by the tag, and a ratio of 1:3 and 1:1 in the lower strand sequence generated by the tag, in addition to the variant nucleotide generated from the target nucleic acid. Employment of identification primers in a primer extension reaction will thus generate signals corresponding to the molar ratios stated above, and will be available for comparison to the identification primer result for the variant nucleotide generated from the target nucleic acid.

In another embodiment, the first and the second identification primers bear a detectable characteristic. The detectable characteristic of the first identification primer may be the same or different from the detectable characteristic of the second identification primer.

In another embodiment of the invention, two or more variant nucleotides are identified. One, both, or two or more of the variant nucleotides can be transversions. The two or more variant nucleotides can be on the same nucleic acid molecule, or they can be on different nucleic acid molecules.

In another embodiment of the invention, the variant nucleotide is a transversion, and the identification primers are extended by one or more labeled nucleotide bases, and are capable of being detected by a characteristic selected from the group consisting of mass, apparent mass, molecular weight, apparent molecular weight, a combination or ratio of mass and charge, number of bases, magnetic resonance, spectrophotometry, fluorometry, electric charge, polarimetry, light scattering, luminescence and antigen-antibody interaction.

In another embodiment of the invention, the variant nucleotide is a transversion, and the identification primers are extended by a chain terminator. The chain terminator may be a dideoxynucleotide or an acyclo terminator. The chain terminator can be labeled with a detectable moiety. Most preferably, the chain terminator is labeled such that it can be detected with a fluorescence detector.

In another embodiment, the variant nucleotide comprises a transversion and the identification primers comprise a tag capture moiety. The identification primers with tag capture moieties may be captured on an array. The array may be an addressable array or a virtual array.

In another embodiment of the invention, the variable nucleotide is a transversion and the second strand amplification primer comprises a 5' tag having the same variant nucleotide, the same invariant nucleotide flanked in the 5' direction, and the same invariant nucleotide flanked in the 3' direction as the first strand amplification primer, and wherein the first strand amplification primer reflects a transversion ratio of 1:1 in the variant nucleotide and wherein the second strand amplification primer reflects a transversion ratio of 1:3 in the variant nucleotide, and wherein at least three identification primers are employed in the primer extension reaction.

In another embodiment, the invention comprises a method of performing primer extension utilizing at least two amplification primers comprising: obtaining a target nucleic acid comprising a variant nucleotide flanked by an invariant nucleotide; hybridizing to the target nucleic acid a first amplification primer having a 5' tag comprising the variant nucleotide flanked by the invariant nucleotide, wherein the 5' tag is substantially unable to hybridize to the target nucleic acid, and a second amplification primer; and extending the amplification primers in the presence of at least one or more nucleotides and a polymerizing agent, thereby performing primer extension.

In another embodiment, the invention comprises a composition, comprising: a primer having a region capable of hybridizing to a target nucleic acid wherein the target nucleic acid comprises a variant nucleotide and an invariant nucleotide, and wherein the primer further comprises a 5' tag region having the variant nucleotide and the invariant nucleotide of the target nucleic acid, and wherein the 5' tag region is substantially incapable of hybridizing to the target nucleic acid under conditions suitable for amplification of the target nucleic acid. Conditions sufficient to achieve amplification are well known in the art and have been illustratively described or incorporated by reference herein. Such conditions include protocols for amplification of target nucleic acids by thermally stable polymerizing agents.

In another embodiment, the invention comprises a method of monitoring the efficiency of incorporation of chain terminators into primers in a primer extension reaction, comprising: generating a population of amplicons from a mixed sample of target nucleic acid, wherein the population of amplicons comprises 5' tag variant sequences at known ratios and target-derived variant sequences at unknown ratios; performing primer extension reactions on the population of amplicons employing chain terminators and employing a population of distinguishable primers specific for the variant sequences present in the 5' tag derived sequences and the target-derived variant sequences; detecting and measuring efficiency of incorporation of chain terminators into the population of primers at the known ratios, thereby monitoring the efficiency of incorporation of chain terminators into primers in a primer extension reaction against the 5' tag derived variant sequences; detecting and measuring efficiency of incorporation of chain terminators into the population of primers at the unknown ratios, thereby measuring the rate of incorporation of chain terminators into primers in a primer extension reaction against the target-derived variant sequences. By a mixed sample is meant that the target nucleic acid comprises nucleic acids from two or more individuals. By a population of primers specific for the known sequences is meant a population of identification primers.

In yet another embodiment, the invention comprises a method of performing a primer extension reaction, comprising: obtaining a sample comprising target nucleic acid from one or more individuals; obtaining an amplicon population having a sequence generated from the sample and a sequence generated from a tagged first strand amplification primer, by amplifying nucleic acids in the sample having a variant nucleotide, wherein the tagged first strand primer is employed that comprises a 5' tag substantially incapable of hybridizing to target nucleic acids in the sample, and wherein the 5' tag contains the variant nucleotide, and wherein a second strand amplification primer is employed; employing the amplicon population in a primer extension reaction wherein the identity of the variant nucleotide in the sequence generated from the sample is determined by hybridizing a first identification primer immediately adjacent to the variant nucleotide in the sequence generated from the sample; hybridizing a second identification primer immediately adjacent to the variant nucleotide in the sequence generated from the amplification primer; extending the first and the second identification primers in the presence of one or more nucleotides and a polymerizing agent; determining the identity of the variant nucleotide generated from the sample; and comparing extension product of the first identification primer and extension product of the second identification primer, thereby performing the primer extension reaction. The variant nucleotide may represent a transversion and may arise due to, for example, an insertion, deletion, rearrangement, or by any other way that variability is introduced into a nucleic acid sequence either naturally or synthetically.

The figures have been simplified for clarity. For example, the extension product of a primer which abuts a variant nucleotide is shown as a single peak in the figures, as would be the case if the variant position were homozygous. If the variant position was heterozygous, two very closely associated peaks may be generated, with the two extension products having very slightly different mass:charge ratios, due to the different terminal base incorporated, and possibly the different labels attached to the terminating base. Differences in 5' tags can alter mass:charge ratios.

As employed herein, "S" refers to a G or a C, "R" refers to an A or a G, "Y" refers to a T or a C, "K" refers to a G or a T and "M" refers to a C or an A.

FIG. 1 illustrates amplification primers having a mirror of the polymorphism in the target nucleic acid. Shown are two amplification primers with tags, where the two primers differ only in the identity of a single nucleotide in the tag, and where the single nucleotide is flanked on either side by the same nucleotides flanking a single nucleotide polymorphism of interest in the target. Bases flanking the 'mirror' polymorphism (in the 5' tag) are identical to those flanking the 'real' polymorphism in the target. One of the amplification primers is modified to have a 5' DNA sequence (shown dotted) largely unrelated to the target DNA template, or any other DNA sequence from the organism from which the target DNA is derived. This amplification primer is in fact a population of two very similar, but distinct sequences, with the primers annealing to exactly the same target (the complement of the solid arrow sequence), but differing from each other in that one single nucleotide in the tail is different. This single nucleotide position 'mirrors' the 'real' SNP polymorphism targeted. When amplification is performed with a combination of the two primers shown, and an opposing primer (not shown) the effect is to generate a pool of amplicons in which a 'copy' of the (heterozygote form of the) 'real' SNP is generated in the terminal end of the amplicons, these 'mirror SNPs' being derived form the 5' tail of these hybrid primers. Note that the base immediately before the SNP and immediately after the SNP are shown, although not specifically identified. It may be that as few as zero bases are required to be copied from the 'real SNP', but it may require more than one base before or after or before and after the SNP to have the 'mirror SNP' behave in the same fashion as the 'real SNP' in respect to relative efficiency of incorporation of chain terminating nucleotides upon a primer extension reaction being performed against both the real SNP and the mirror SNP.

Figure 2:
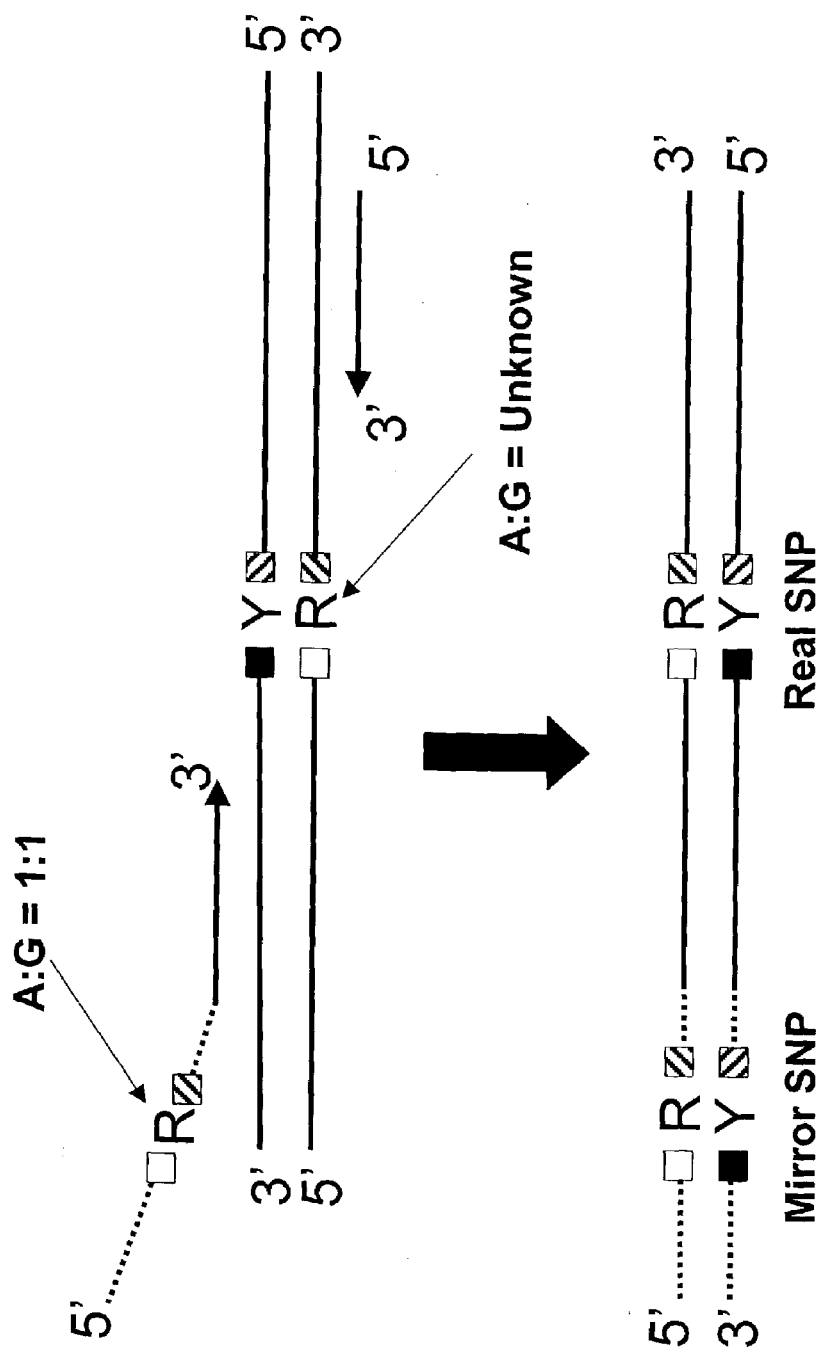
FIG. 2 illustrates a diagnostic amplification of a target nucleic acid sequence comprising a single nucleotide polymorphism, and the amplicon that would result.

FIG. 2 illustrates a diagnostic amplification of a target nucleic acid sequence comprising a single nucleotide polymorphism, and the amplicon that would result. In this embodiment, at least three different amplification primers are employed to amplify a target nucleic acid comprising a polymorphic nucleotide, such that the polymorphic nucleotide is included in the resulting amplicon. Two of the primers, as illustrated, will have 3' ends of identical sequence capable of hybridizing to the target nucleic acid at the same sequence, for which they compete equally, so as to amplify the region of the target nucleic acid having the polymorphism in it, and will have a 5' tag sequence largely incapable of hybridizing to the target sequence. This 5' tag sequence is shown to contain an 'R', representing that both G and A bases are present at this position, and that this is the only difference in the sequence of the 5' tag. The third primer, also shown, will hybridize to the other strand of the duplex distal to the polymorphism, so that the amplicon will contain the polymorphism of interest. To further clarify, the two primers that hybridize to the same sequence in the target have 5' tags that are substantially incapable of hybridizing to the target nucleic acid under the conditions of the amplification reaction and differ only in a single nucleotide residue in the 5' tag. These primers bear the image of the targeted polymorphism in their 5' tail. In this embodiment, the A and G in the tags are also flanked with the same nucleotides that will flank the targeted polymorphism in the amplicon. The employment of primers such as those described above affords the ability to amplify a target nucleic acid so as to generate an amplicon having a "mirror SNP" generated through judicious selection of the 5' tags wherein the "mirror SNP" is generated in a known and controlled ratio. In one embodiment, the tagged primers are preferably employed in equal ratios in order to generate an amplicon wherein the A:G ratio in the resulting population of amplicons is 1:1, mimicking a heterozygous site on the same amplicon as the polymorphic site amplified from the target nucleic acid. An illustration of this embodiment is shown in FIG. 2, where the A:G ratio generated by the 5' tags of the primers is referred to as a "mirror SNP," and the polymorphic site amplified from the target nucleic acid is referred to as a "real SNP." As can be seen in this embodiment, each mirror and real SNP resides in the same sequence context in that the bases flanking each mirror and real SNP are identical. This embodiment provides an advantage in that heterogeneities in primer extension reactions carried out at these sites that may be due to sequence context differences are advantageously reduced. Further, this embodiment is particularly advantageous in that the signal generated from the mirror SNP should provide an observer with a clear heterozygote signal following a single base primer extension reaction. The generation of a reliable heterozygote mirror SNP allows for the assessment of the situation at the targeted real SNP, giving a reference point as to the efficiency of incorporation of a G terminator and an A terminator where each template is in equivalent abundance. The examination of the relative efficiency of incorporation of the terminating bases following primer extension against the real SNP present in the amplicon allows determination of the zygosity of this polymorphism, that is whether it too is a heterozygote, or is significantly skewed towards incorporation of one or other of the bases exclusively, as would be expected of a homozygote SNP.

FIG. 3 illustrates the products of a 50:50 diagnostic amplification and shows how the lower or upper strand may be employed in a diagnostic primer extension reaction. FIG. 3 illustrates an embodiment wherein an amplicon has been generated having a mirror SNP and a real SNP. The mirror SNP and real SNP are present on the same amplicon and are therefore in molar equivalence, regardless of the efficiency of the PCR reaction. Both positions can be interrogated simultaneously in using distinct and distinguishable SNP-IT™ primers which must hybridize to the same strand, so that the sequence context around the SNP is maintained between the mirror SNP and the real SNP, and so that any influence this sequence context might have on the efficiency of incorporation of one chain terminating nucleotide over the other might be normalized between the mirror and real SNP interrogations. Note that if interrogating the mirror and real SNPs as an addition of C and T terminators from the upper strand (the extension product of the tag tailed primer), the excess amplification primer should be efficiently removed (by, for example, Exo I digestion) prior to the SNP-IT™ extension reaction. Failure to do so may result in the excess primer being available to act a template during the SNP-IT™ extension reaction, and loss of the 1:1 molar ratio of the mirror:real SNP. Interrogation of the mirror SNP and real SNP as addition of an A and G terminator on the lower (daughter) strand of the hybrid primer avoids this problem, but requires that sufficient DNA sequence is provided 5' of the mirror SNP position in the hybrid primer to allow stable hybridization of a SNP-IT™ primer on the daughter strand. Note that the terminal 3' base in the extension primers is shown to be identical to the base immediately preceding the mirror and real SNP in the appropriate direction, and that the base beyond the variant nucleotide is also maintained between mirror and real SNP in this example.

Figure 4:
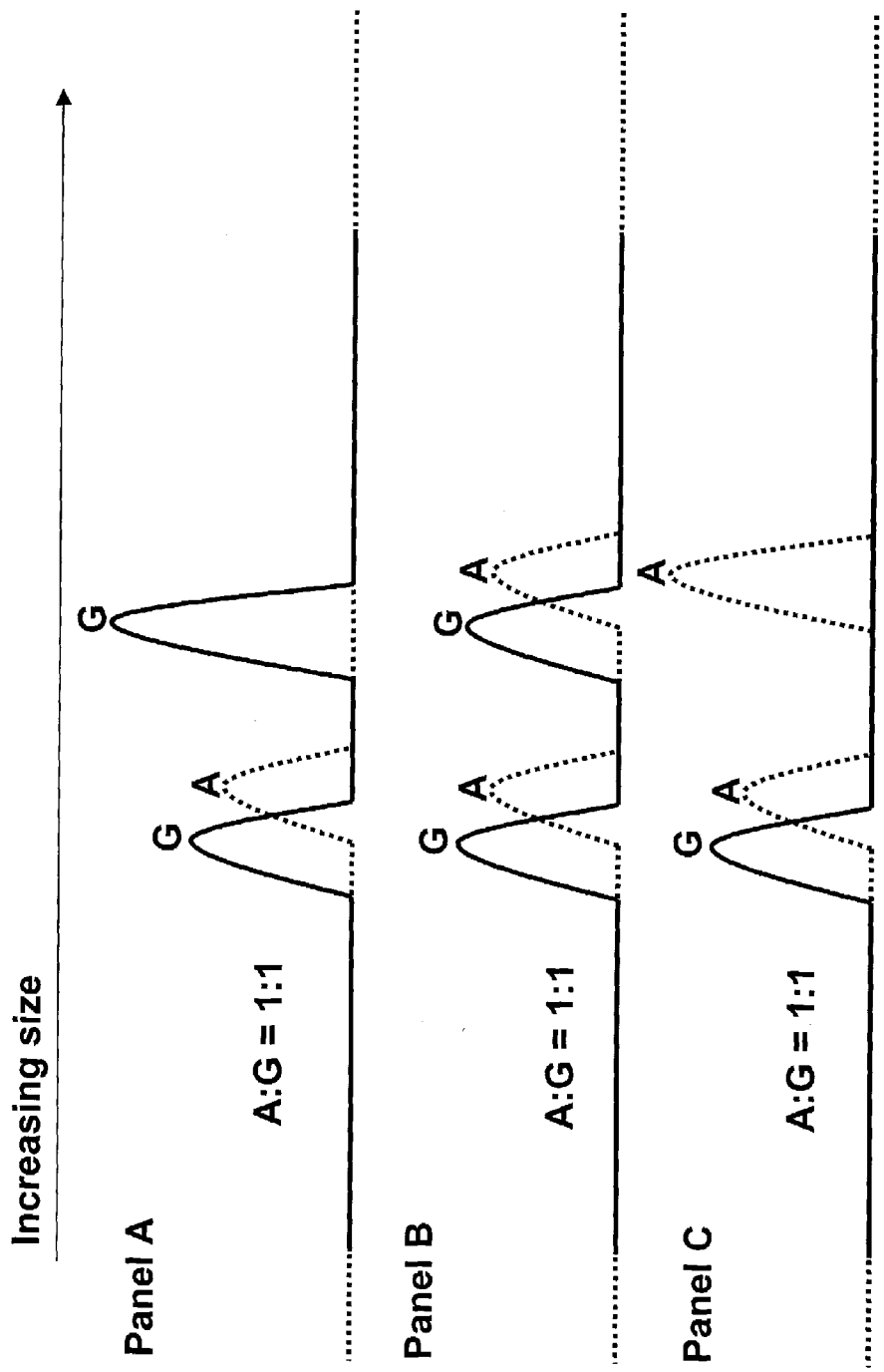
FIG. 4 illustrates three possible outcomes where the target comprises a single source of template DNA, employing an A/G single fluorescent base extension reaction and analysis by capillary electrophoresis for illustration only.

FIG. 4 illustrates three possible outcomes where the target comprises a single source of template DNA, employing an A/G polymorphism for illustration only. Panel A results where the target SNP is homozygous GG; Panel B results where the target SNP is heterozygous AG; Panel C results where the target SNP is homozygous AA. The mirror SNP and real SNP are present on the same amplicon and are therefore in molar equivalence, regardless of the efficiency of the PCR reaction. Both positions can be interrogated simultaneously by using distinct and distinguishable SNP-IT™ primers which hybridize to the same strand, so that the 'sequence context' around the SNP is maintained between the mirror SNP and the real SNP, and so that any influence this sequence context might have on the efficiency of incorporation of one chain terminating nucleotide over the other might be normalized between the mirror and real SNP interrogations. It is not an absolute requirement that the signal strength between the mirror SNP heterozygote and the real SNP result are of equivalent intensity, although this would be the most advantageous situation. It is only necessary that there be sufficient signal intensity at the mirror and the real SNP that a ratio between the heterozygote peaks at each can be determined which is above the level where stochastic fluctuations and artifactual noise may account for a significant portion of the detected signal. It may also be advantageous to set an acceptable level of signal detection from the (artificial) mirror SNP before any result from the associated real SNP is taken as valid. This may be of particular utility in multiplex analyses where failure of one specific amplicon to amplify to acceptable levels could be ascertained by examining the signal from that amplicon's mirror SNP.

Figure 5:
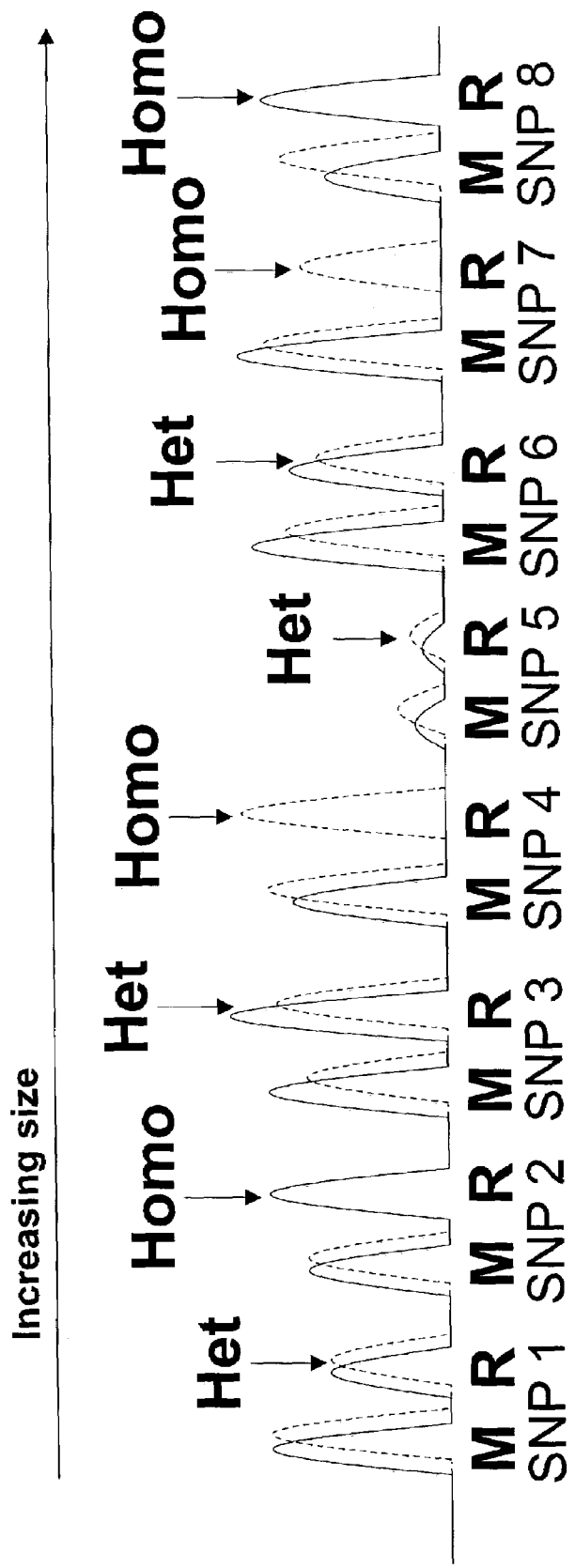
FIG. 5 illustrates how outcomes may appear in a multiplex assay of eight polymorphisms, with the mirror SNPs for each target SNP represented as the smaller doublet peaks.

FIG. 5 illustrates how outcomes would appear in a multiplex assay of eight polymorphisms from a single source template DNA. For any given amplicon, assayed at both the mirror (M) and real (R) SNP, there are only three possible outcomes for the real SNP, given that we have single source template DNA. The mirror SNP will always return a heterozygous signal, given that this amplicon has been produced to assayable levels within the multiplex, and the ratio of incorporation of one nucleotide over the other will be measurable in some fashion, although the absolute level of incorporation may differ from M to R (despite their molar equivalence), and from individual SNP to SNP. The signal returned by the real SNP will either be very close to this heterozygote signal ratio, or is will be severely skewed to one or other side of the ratio, indicating that the real SNP was a homozygote of one or other flavor. By flavor is meant the type of SNP, which will be one of the six different combinations that are possible (AG, AC, AT, TG, TC, GC) The signal returned in this case may also be larger than that returned by the mirror SNP, although not necessarily so, given that the SNP-IT™ primers used to interrogate the mirror and real SNPs may have differing hybridization characteristics. However, the ratios between peaks generated from mirror and real SNPs will be comparable, given that all experimental variables and sequence context variables are automatically normalized using this described system of analysis. A panel of eight unidentified SNPs has been used here for demonstration only. Note that SNP 5 is shown to have generated particularly weak signals for both the mirror and the real SNP, as might be expected if the targeted amplicon had failed to generate effectively in the multiplex analysis. Taking a ratio from such results will be more prone to error in the ratios generated. This system would be applicable to any SNP panel, or any mixture of different SNPs, given that each of the nucleotide species used as a terminator has a distinguishable characteristic. Also, the signal returned is shown as peaks, perhaps on a capillary electrophoresis instrument where the real SNP SNP-IT™ primer migrates more slowly than the mirror SNP primer, and the terminating nucleotides carry some detectable label, such as a fluorescent dye. The mirror SNP heterozygote result is shown proximal to the corresponding real SNP result, but it need not be the case that mirror and real SNP results are close to each other like this, only that they are distinct. It is clear that any system which can discriminate between the products of the SNP-IT™ reaction would be applicable to the technique.

Figure 6:
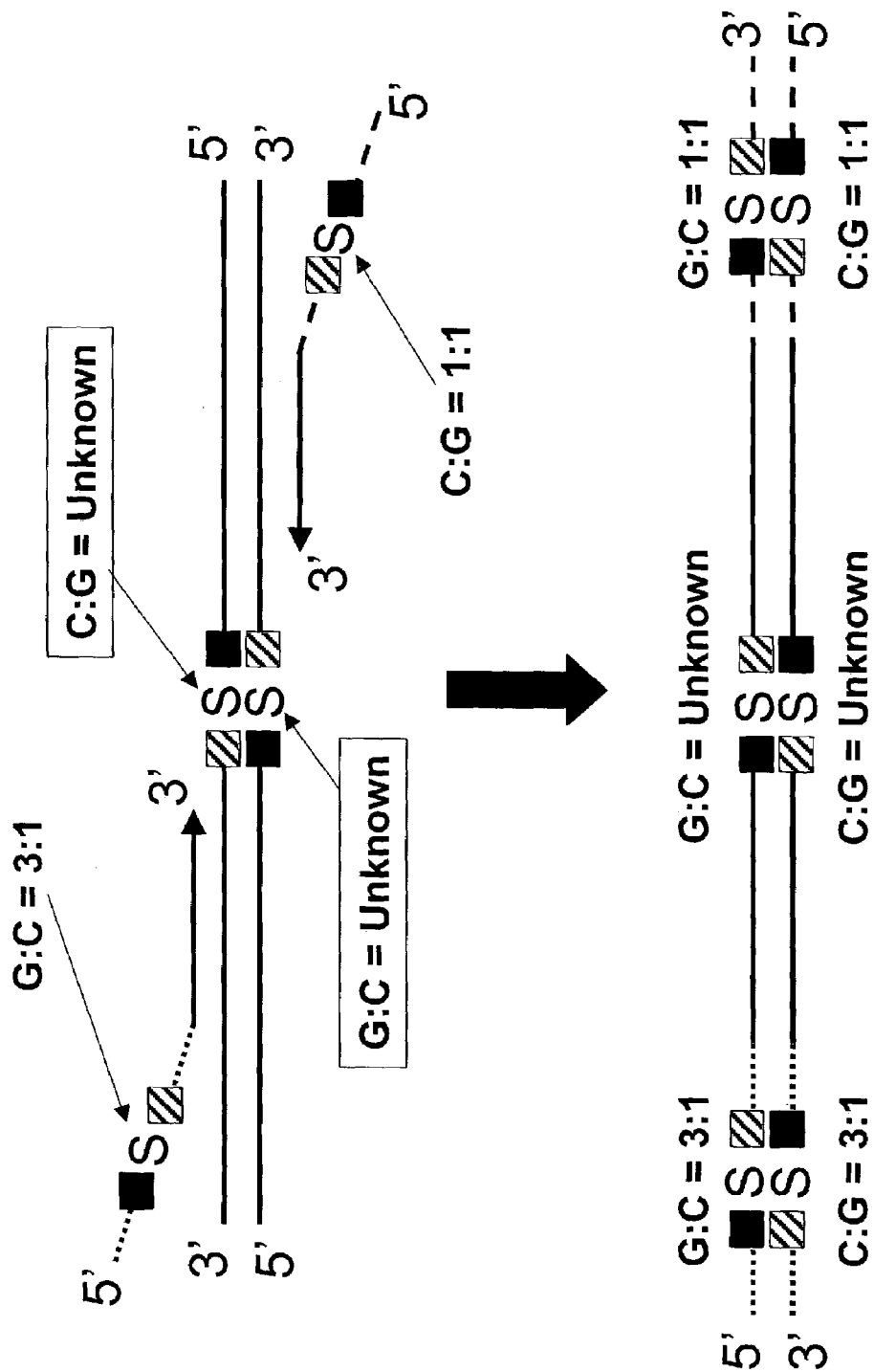
FIG. 6 illustrates a single tube test for a mixed sample for resolving polymorphisms that are transversions flanked on either side by nucleotides that are complementary to one another. Solid box indicates a nucleotide complementary to hatched box.

FIG. 6 illustrates a single tube test for the interpretation of a possible mixed DNA sample, targeting a polymorphism that is a transversion flanked on either side by nucleotides that are complementary to one another. Solid box indicates a nucleotide complementary to hatched box. The ratios shown and the use of G/C are for example only. One skilled in the art will understand that any transversion and any ratio could be used in this assay. Also, only a single flanking nucleotide is shown around the real and mirror SNP. This is for clarity only in the diagram. It may be that more than one nucleotide on one or other or both sides of the SNP are required to give the same efficiency of incorporation of the terminating bases upon primer extension, or that as few as zero bases need be complementary. Note that the ratio of 3:1 (G:C) on the forward primer shown is achieved by carrying out the initial PCR reaction with the forward primer bearing the G at a concentration 3× higher than the forward primer bearing a C. This ratio is reversed on the daughter strand, as there will be 3× as much C on the daughter strand as there will be G. The reverse primer is also shown as a mixed population of two primers differing only in the identity of a single nucleotide. Here the ratio of G-bearing primer to C-bearing primer is controlled in the initial PCR to be equivalent, generating a mirror SNP in the amplicon at 1:1 ratio. Note also that the bases around both the artificially introduced polymorphic site are reversed to maintain the sequence context of the mirror SNP, matching the real SNP.

Figure 7:
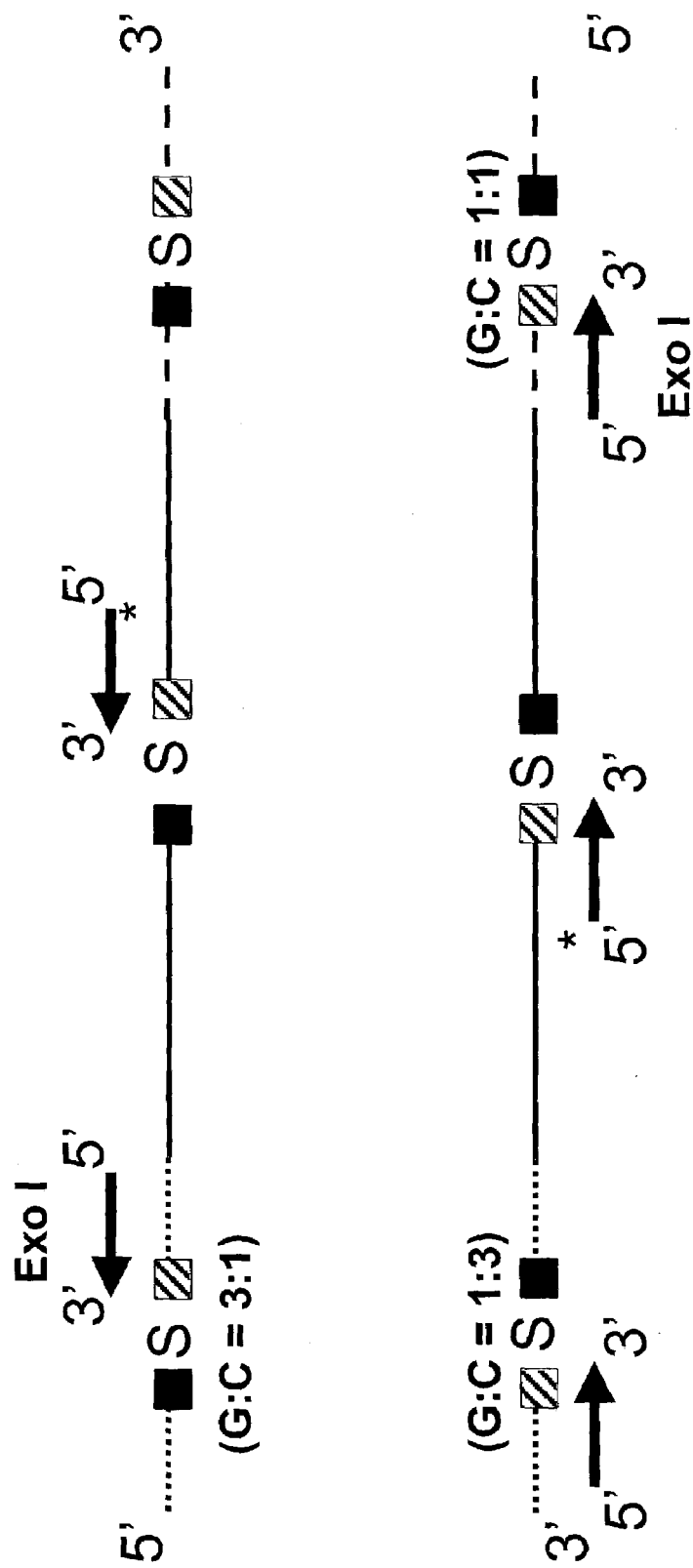
FIG. 7 illustrates a quadruplex reaction wherein the amplicon generated in FIG. 6 is interrogated by four distinct extension primers and are used to generate data from three ratios of G:C and an unknown polymorphic residue S.

FIG. 7 illustrates a quadruplex reaction wherein the four extension primers are used to generate data from three know ratios of G:C and a polymorphic S residue of unknown ratio. The known ratios of G:C are 3:1, 1:1, and 1:3. Either, but not necessarily both, of the real SNP S primers is required. A single asterisk indicates that only one of the primers so marked is necessary, and one of these primers may be judged to have preferable sequence characteristics over the other, and therefore be the preferred choice in a primer extension reaction. The primers marker Exo I indicate that these primers should only be used given the efficient removal of the complementary initial amplification primer prior to the identification step. Note that the 1:1 polymorphism could also be interrogated on the other strand (primer not shown) but this would necessitate that a larger 5' tag sequence be used on the initial amplification primer, to give sufficient template DNA in the amplicon to support stable hybridization of the primer extension primer. In order to both generate data on the three ratios of G:C produced (3:1, 1:3 and 1:1) and information on the real SNP, one need only use four extension primers, as shown. The use of only four extension primers will reduce the analysis required, and increase the potential to multiplex the analysis of different SNPs, with each SNP requiring the analytical 'space' (be it on a capillary, or other analysis readout platform) to fit all the different extension products whilst maintaining their distinct identification from each other. Note that regardless of the extension primers used, the terminal 3' base of all primers is demonstrated to anneal to a 'hatched box' nucleotide, which is the complementary base of the 'solid box' nucleotide. As demonstrated, the sequence context around the targeted SNPs is maintained regardless of which strand is being utilized as template during the identification reaction.

Figure 8:
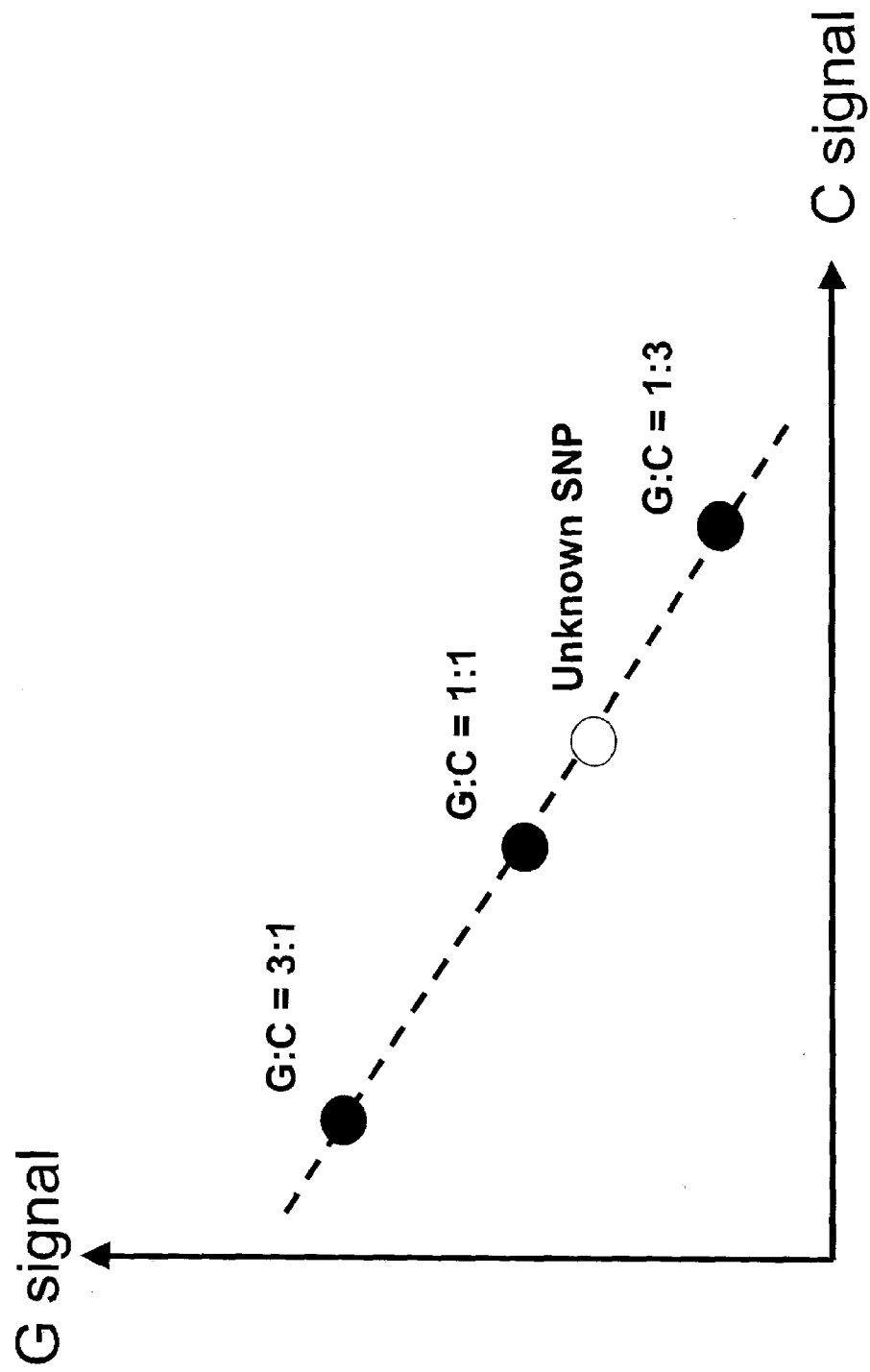
FIG. 8 illustrates how results from a quadruplex single tube G:C (3:1, 1:1 and 1:3) assay would ideally appear given that the primer extension reaction is sub-saturating with respect to the terminating nucleotides

FIG. 8 illustrates how results from a quadruplex single tube G:C (3:1, 1:1 and 1:3) assay would ideally appear. A graph of relative efficiency of incorporation of the X and Y terminators (here shown as G and C) may be generated, and the observed efficiency of incorporation at the 'real SNP' placed somewhere on this graph, indicating the relative proportions of the X and Y nucleotide that must have existed in the template DNA used to seed the reaction. This graph is for illustrative purposes only, as it is unlikely that the graph generated by this technique will in fact be a straight line as shown, particularly if the primer extension reaction has been allowed to proceed to the point of saturation (that is where some necessary component of the primer extension reaction has been exhausted).

Figure 9:
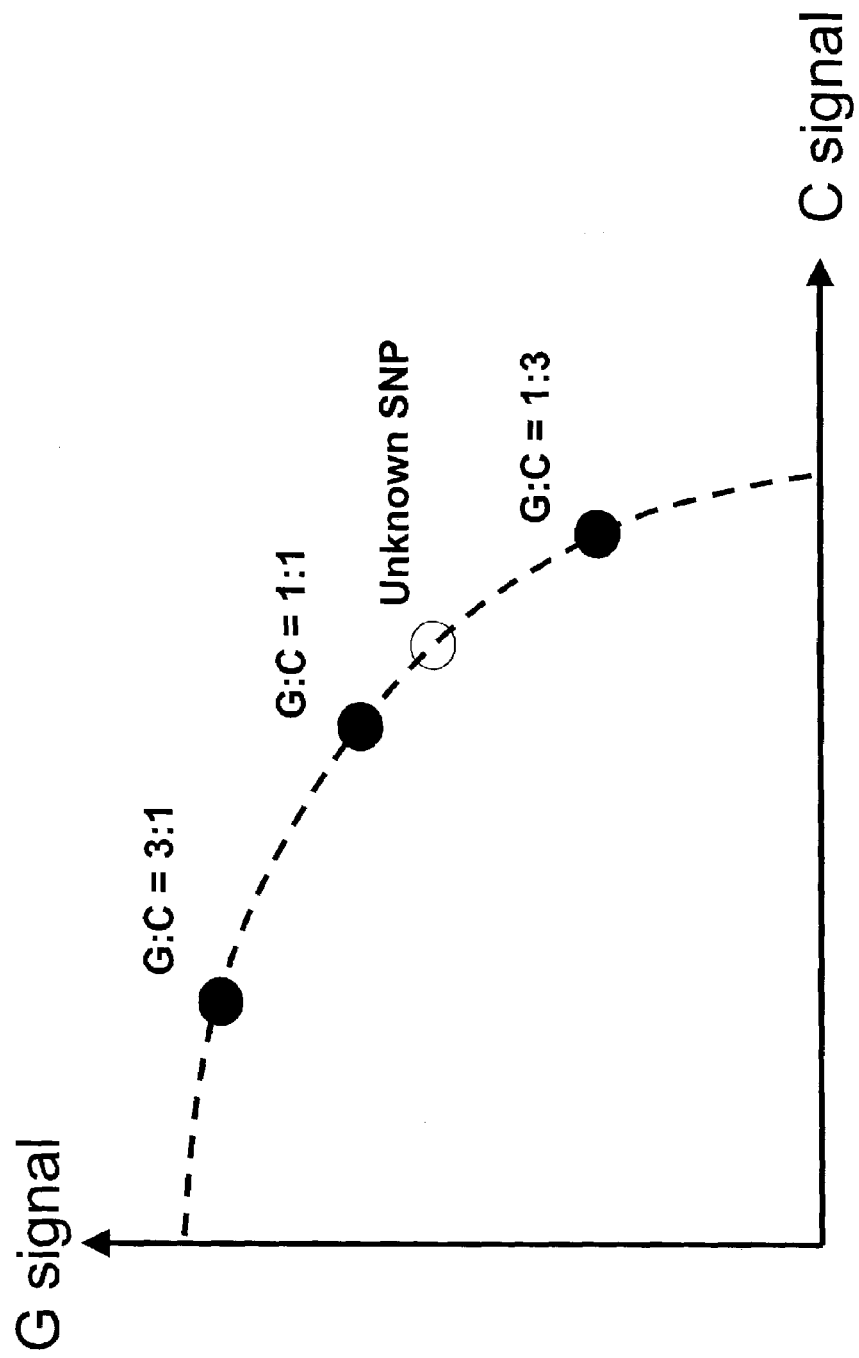
FIG. 9 illustrates the likely shape of the graph of relative incorporation of two terminating nucleotides in a primer extension reaction.

FIG. 9 illustrates the more likely shape of the graph of relative incorporation of two terminating nucleotides in a primer extension reaction. The graph contacts the axis at the two extreme points of homozygosity, and presumes that even at these points, the quantity of amplicon being analyzed is equivalent. It will be the case that for each individual SNP there will be a specific mathematical function which describes the shape of the curve, and this shape will be derived empirically for each SNP flavor in a necessarily limited number of local sequence contexts.

Figure 10:
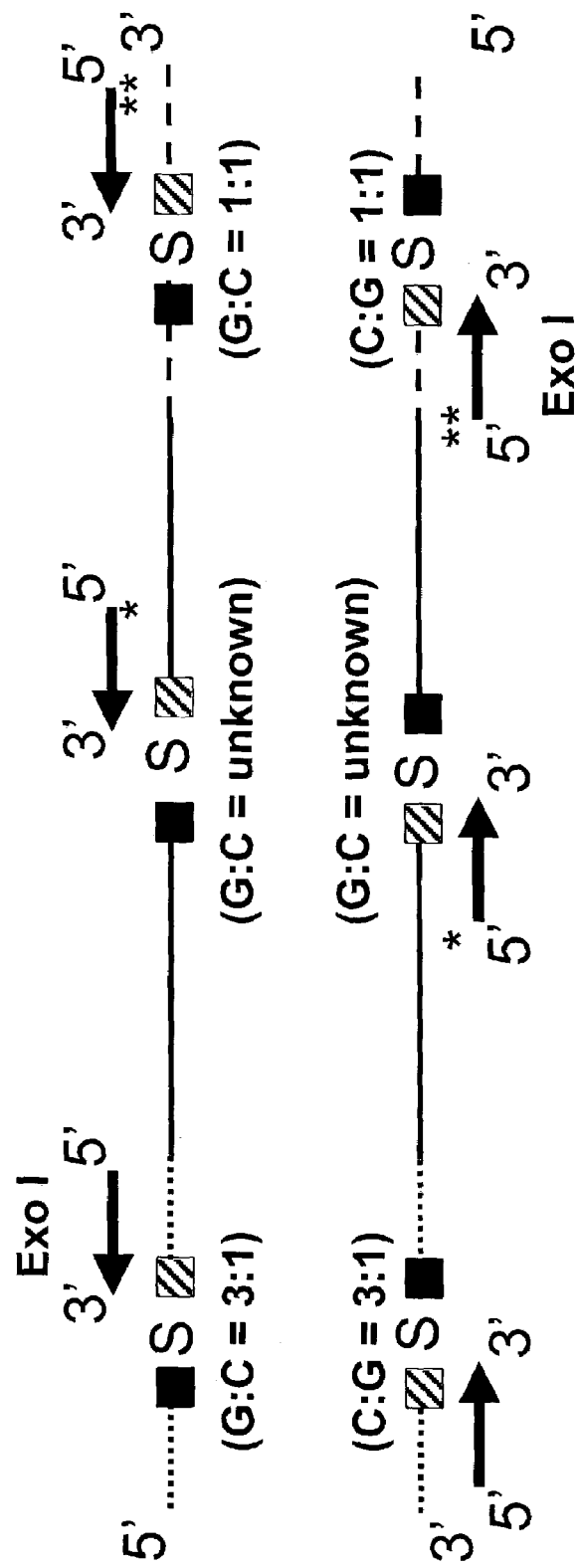
FIG. 10 illustrates the assay of a transversion polymorphism with up to six extension primers per amplicon.

FIG. 10 illustrates how a transversion polymorphism can be assayed with up to six extension primers in a single tube. A single asterisk indicates that both of these target identification primers may be used, and their results averaged, giving careful consideration to the fact that in a homozygote, or mixed, sample one or other of these results must first be changed to the reciprocal value, as any skewed value will be reversed on the opposite strand. A double asterisk indicates that both of these tag identification primers may be used, and their results averaged, as these do represent a true balanced heterozygote when assayed on either strand. Primers labeled Exo I should only be used if amplification primers are efficiently removed prior to the use of the primers labeled Exo I. It is possible to analyze the three different SNPs with up to 6 SNP-IT™ primers, analyzing each on both the upper and lower strand. Where the mirror SNP has generated a ratio switch on the other strand, this must be analyzed on both strands in order to generate information on the efficiency of terminator X an Y at both ratios. However the other mirror SNP, generated from the other amplification primer will not undergo this ratio switch when it is duplicated. It will merely reproduce a copy of itself at 1:1 ratio again. These two 1:1 ratios could be analyzed on both strands using two distinct SNP-IT™ primers, and the efficiency of incorporation of the X and Y terminators averaged between the two extension reactions. Similarly, the 'real SNP' could also be analyzed on both strands, and a consensus of the ratio of X and Y generated, bearing in mind that this will switch from strand to strand given that the 'real SNP' is imbalanced as a result of being a mixture of more than one template. Mathematical correction of such an observed switch should be done before a consensus ratio is calculated.

Figure 11:
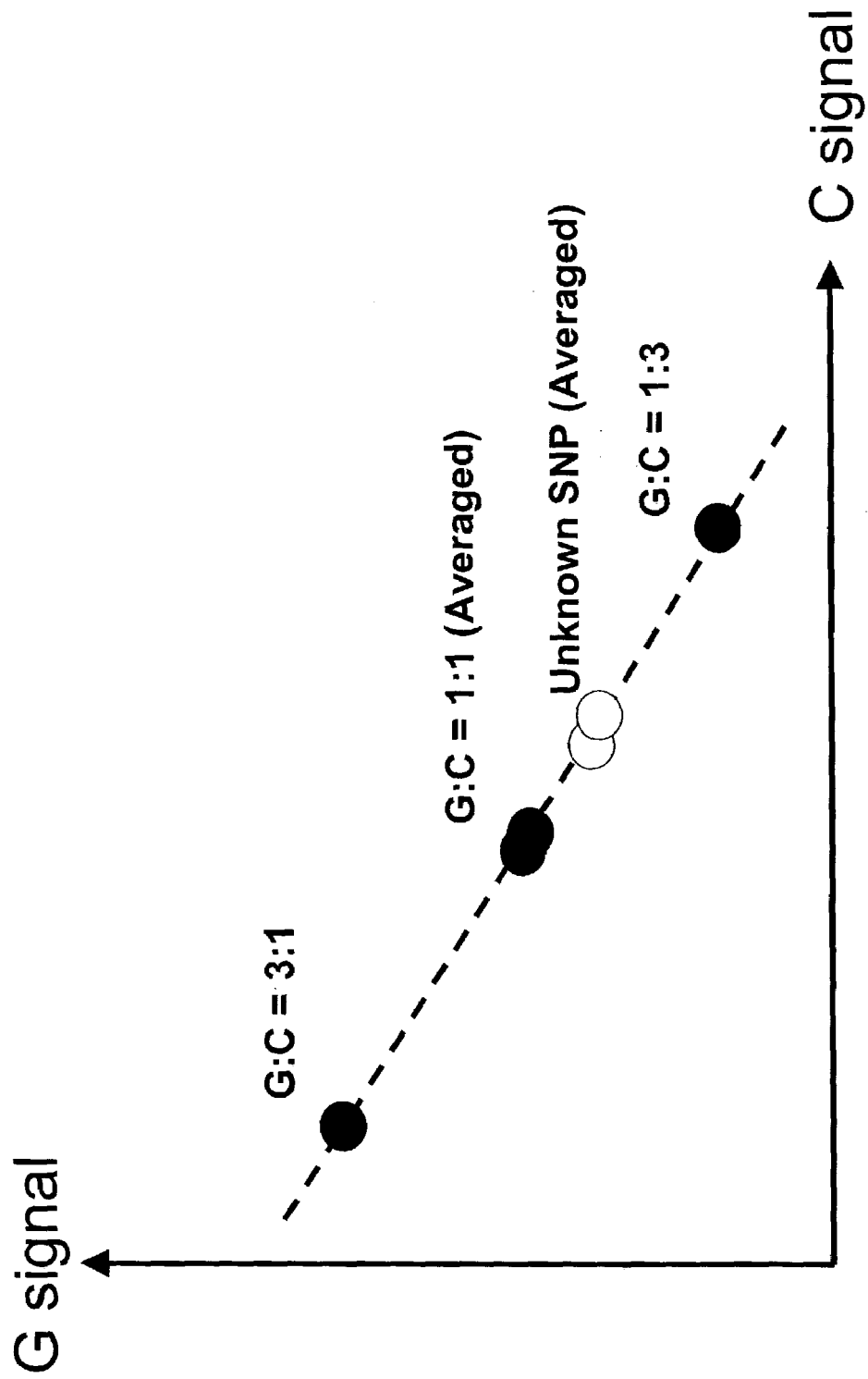
FIG. 11 illustrates how results of a hexaplex one-tube SNP ratio matrix might appear.

FIG. 11 illustrates how results of a hexaplex one-tube SNP ratio matrix might appear. A graph of relative efficiency of incorporation of the X and Y terminators (here shown as G and C) may be generated, and the observed efficiency (average) of incorporation at the 'real SNP' placed somewhere on this graph, indicating the relative proportions of the X and Y nucleotide which must have existed in the template DNA used to seed the reaction. Note also that the efficiency of the 1:1 'mirror SNP' is an average, although to emphasize this point both the 1:1 mirror SNP and the 'real SNP' points are shown as two closely associated points on the graph. This graph is for illustrative purposes only, as it is unlikely that the graph generated by this technique will in fact be a straight line as shown.

Figure 12:
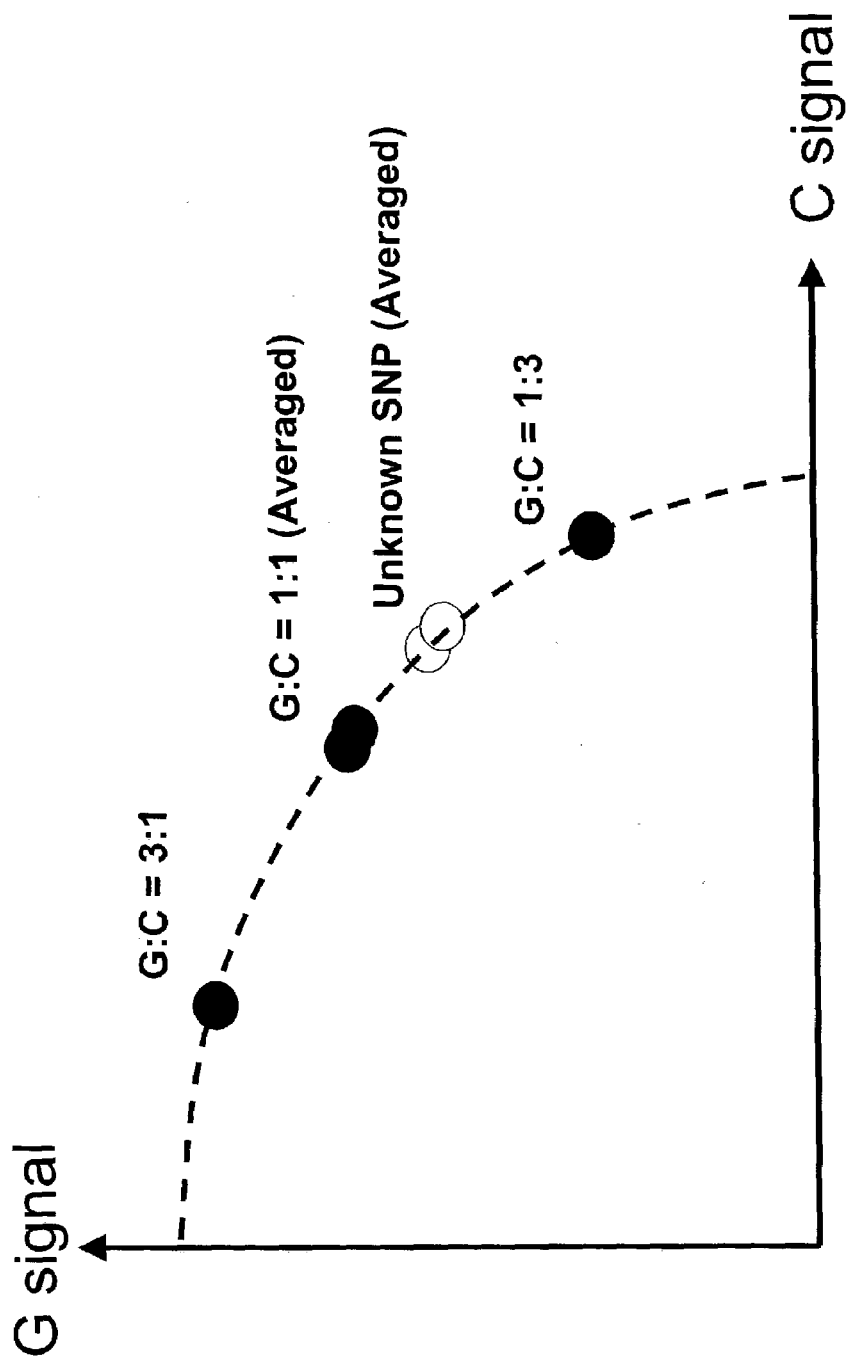
FIG. 12 illustrates the more likely shape of the graph of relative incorporation of two terminating nucleotides in a primer extension reaction.

FIG. 12 illustrates the more likely shape of the graph of relative incorporation of two terminating nucleotides in a primer extension reaction. The graph contacts the axis at the two extreme points of homozygosity, and presumes that even at these points, the quantity of amplicon being analyzed is equivalent. It will be the case that for each individual SNP there will be a specific mathematical function which describes the shape of the curve, and this shape will be derived empirically for each SNP flavor in a limited number of local sequence contexts. Note that the 1:1 ratio and the real SNP analysis can be averaged is analyzed on both strand, and taking appropriate remedial action to account for any deviation from 1:1 ratio which might be encountered at the template derived real SNP. These points are shown as closely associated points to emphasize this point only.

Figure 13:
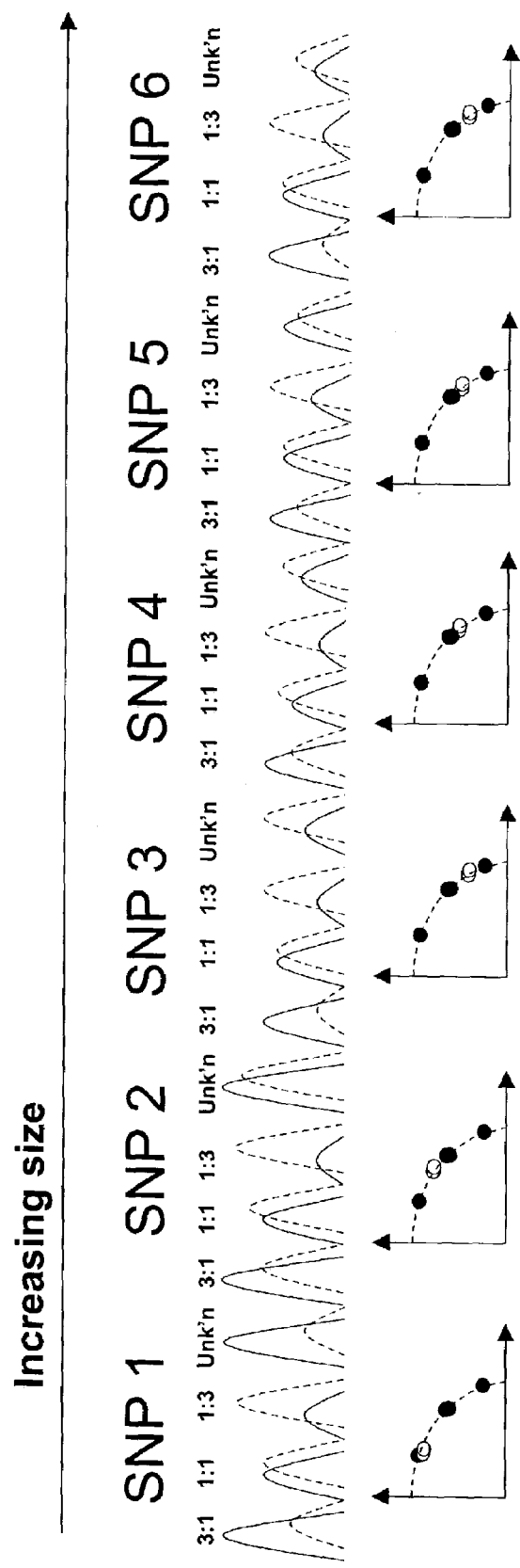
FIG. 13 illustrates how results from a multiplex reaction assaying a plurality of polymorphisms would appear.

FIG. 13 illustrates how results from a multiplex reaction assaying a plurality of polymorphisms would appear. In the case illustrated, six polymorphisms are analyzed using four extension primers per SNP, three interrogating the known ratio mirror SNPs and one interrogating the real SNP. As before, it will be possible to carry out multiplex analysis of many 'real SNPs' at once, whilst generating a standard curve or other mathematical predictor for each, and reading the relative proportions of the X and Y nucleotides from the individual graphs (where X and Y represent the two nucleotide species possible for any individual SNP). By combining the information from many different SNPs co-analyzed in this manner, it will be possible to come to a consensus as to the proportions of individual DNA templates present in a mixture, and this will be facilitated if one of the individual's DNA profiles is know (for example, the profile of the victim of a sexual assault).

Figure 14:
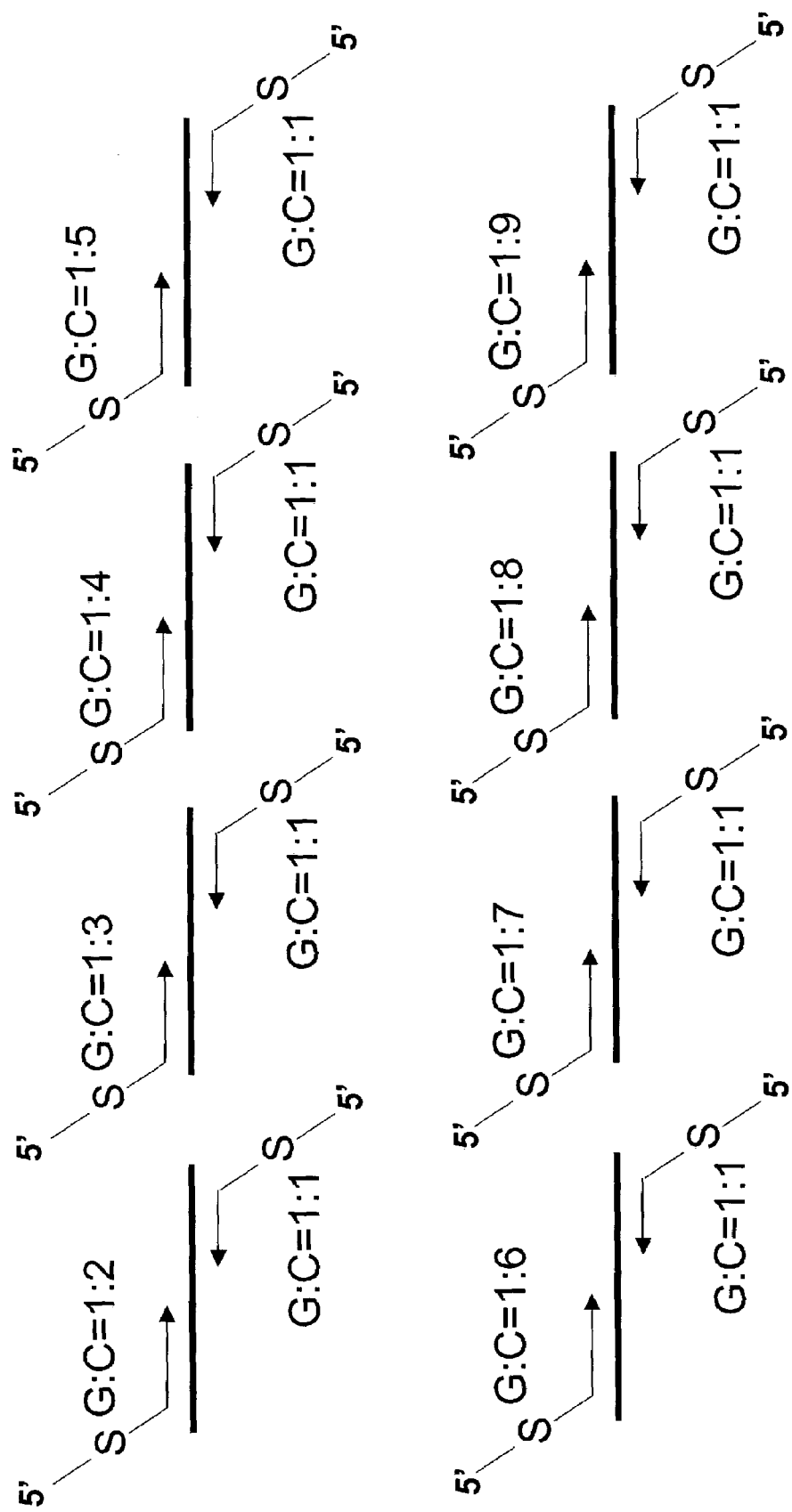
FIG. 14 illustrates a means of defining a mathematical function between the ratio of incorporation of one nucleotide over the other in a primer extension reaction for a given SNP in a specific sequence context.

FIG. 14 demonstrates an alternative and most preferable empirical means of defining a mathematical function between the ratio of incorporation of one nucleotide over the other in a primer extension reaction for a given SNP in a specific sequence context. Illustrated are eight different ratios of a transversion SNP introduced into both terminal ends of an amplicon population through an amplification reaction, although the actual ratios used may be more or less extensive than those shown here. These differing ratios permit the plotting of a relationship between actual level of incorporation, and the known ratio of availability of template DNA. It may not be possible to carry out these various ratio checks in a single tube assay, and for this reason, a 1:1 ratio control is incorporated into the amplicon populations to verify that the level of incorporations here is the same, and that the results from the various skewed mirror SNPs can be assembled together into a mathematical relationship. It may be that having completed this work for one SNP, the mathematical relationship will be applicable to all SNPs flanked by specific sequences, and it may be that this work will have to be repeated for each SNP flavor in all local sequence environments. This will be a necessarily limited number of experiments.

FIG. 15 illustrates the simplest relationship between efficiency of incorporation of two chain terminating nucleotides, which is a linear relationship, and also a more complicated mathematical relationship in the form of a logarithmic/linear relationship. Other mathematical functions, such as exponential functions may also describe the efficiency of incorporation of chain terminating nucleotides at specific ratios, and these may be determined empirically for each specific SNP flavor in a specific local sequence context. Converting the relationship to a linear relationship facilitates the determination of an unknown ratio from an observed ratio of incorporation of terminating nucleotides.

Figure 16:
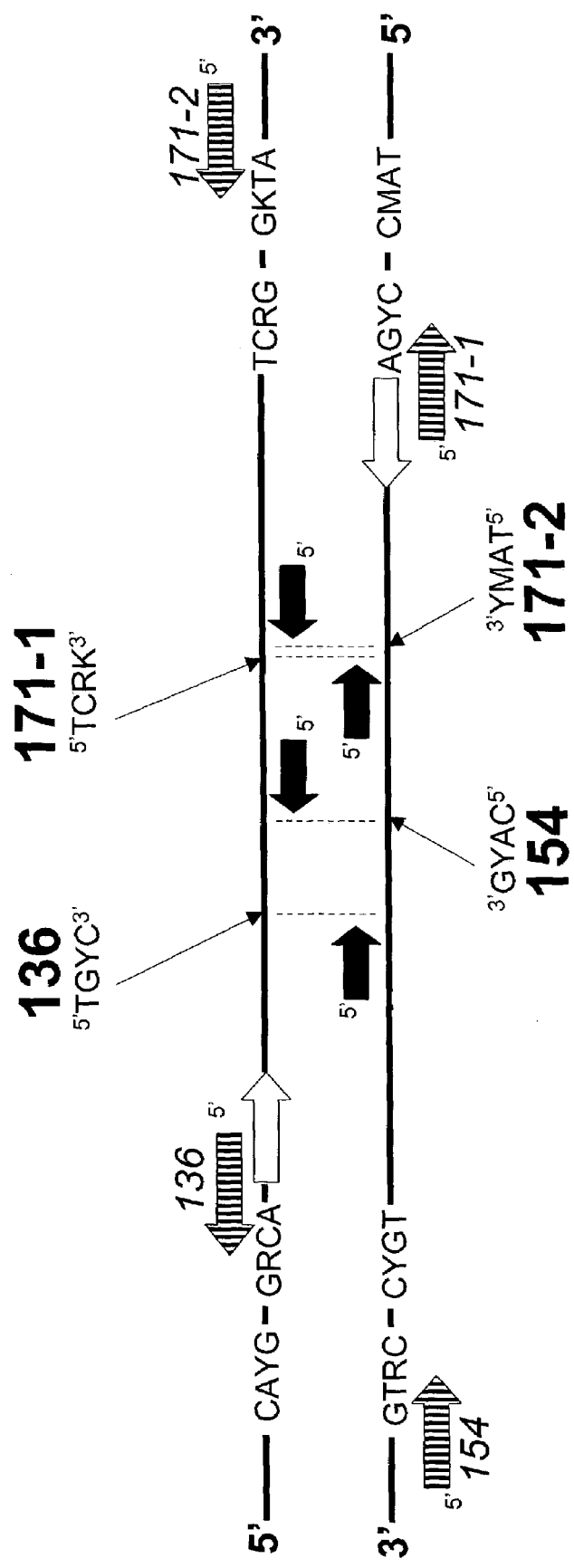
FIG. 16 illustrates an application of the invention to the ovine PrP gene.

FIG. 16 illustrates a practical example of the invention described. The diagram illustrates the amplification of a portion of the ovine PrP gene using initial amplification primers (block arrows) which flank 4 polymorphic nucleotides at positions 136, 154 171-1 and 171-2. These polymorphic nucleotides are re-created upon amplification by virtue of the attachment of 5' tag sequences to the initial amplification primers. Each primer re-creates two of the polymorphic nucleotides (136 and 154 in the tail of the forward primer, and 171-1 and 171-2 in the tail of the reverse primer). Each of the polymorphic sites is re-created as a balanced heterozygote as a result of use of equimolar amounts of the initial amplification primers (a total of two distinct forward primer sequences, and two distinct reverse primer sequences). Only the local sequences around the genuine and re-created heterozygote sites are shown (2 bases 3' and 1 base 5', with respect to the amplicon target of the primer extension reaction). The genuine polymorphic sites are interrogated as shown using four primers (solid block arrows, 5' end only indicated) whereas the re-created balanced heterozygotes are interrogated by a distinct set of four primers (hatched block arrows). Each pair of interrogating primers are distinct, but share commonality over the terminal two bases at their 3' ends. Note that the primers interrogating the re-created 136 and 171-1 polymorphic sites are complementary to a proportion of the block arrows (the template-specific portions of the initial amplification primers). This is a means of limiting the necessary length of the 5' tag sequence required, which benefits the efficient synthesis of these elongated hybrid primers. Note also that due to the nature of the 171-1 and 171-2 polymorphisms (these sites are immediately adjacent), it is not possible to have these re-created sites completely reflect the real situation with respect to the single nucleotide 5' of the polymorphic site being interrogated. Here, the more common of the two possible bases has been indicated in each case. None of the primer extension probes shown indicate any 5' modifications, such as poly T mobility modifiers, which can be used to affect the position to which the various species migrate under electrophoresis. These modifiers are omitted from the diagram for clarity.

Figure 17:
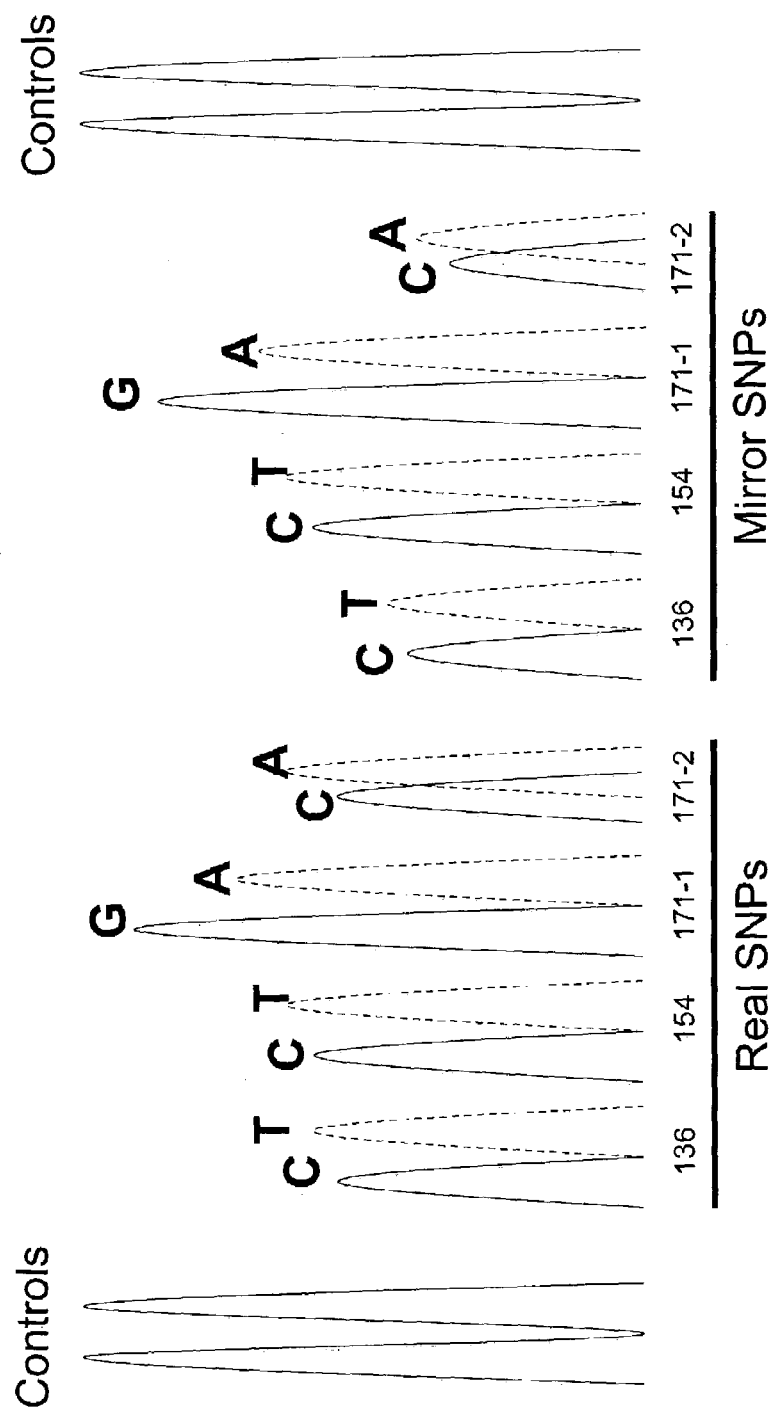
FIG. 17 illustrates output from an ovine PrP analysis if each SNP were a heterozygote, which is not thought to occur in nature.

FIG. 17 illustrates the output from an analysis of ovine DNA as in FIG. 16, but indicates each of the real SNPs as a heterozygote: something which is not expected to occur in nature. The ratio between each of the nucleotides incorporated at the mirror SNP can be compared to the ratio observed at the real SNP, and judgment made as to whether this ratio is indicative of a balanced heterozygote at the real SNP, or if there is a distortion which may indicate the presence of additional copies of the PrP gene in the original template. Note that the mirror SNPs are shown running more slowly (with greater apparent molecular mass) than the real SNP extension products. This need not be the case, so long as each species is uniquely identifiable. Further note that the absolute areas between the real and mirror SNPs need not be the same, but merely the ratio of the areas between the incorporated terminators at any given heterozygote pair. Sizing controls are also indicated in this representation.

Figure 18:
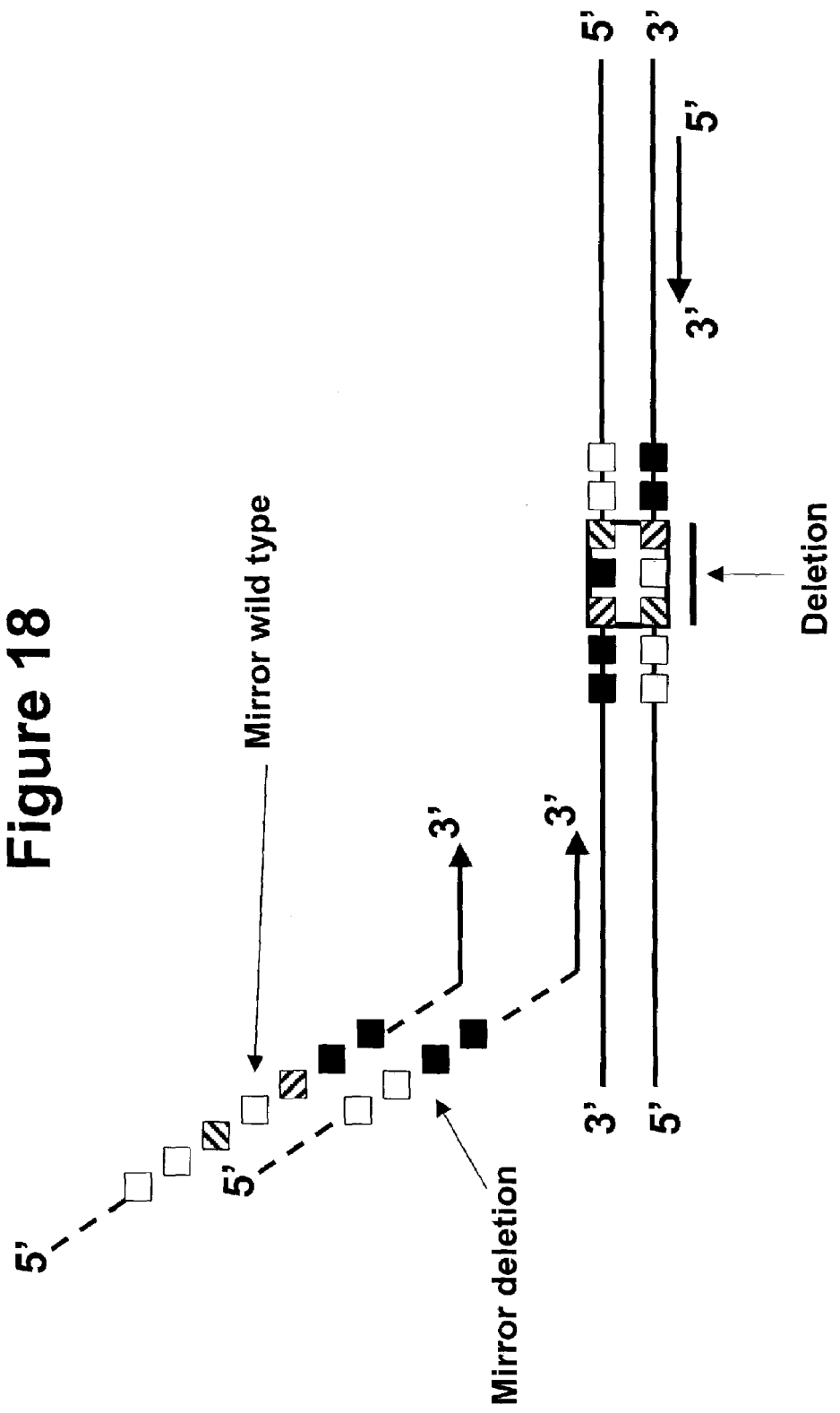
FIG. 18 illustrates how the system would amplify a target nucleotide in which the variant nucleotide arises as the result of a deletion.

FIG. 18 illustrates that the described system can be used to monitor for the presence of a deletion as the variant nucleotide. The product produced from this amplification is limited to show the generation of a product which contains the targeted deletion, but may also be used to generate a population of amplicons in which both the deletion and the wild type target DNA are equally represented. This can be achieved by combining equivalent concentrations of initial amplification primers with the deletion and the wild type sequence represented in the 5' tag sequence. The primer used to probe this artificial representation of the variant nucleotide could be targeted to extend against a nucleotide within the deleted sequence, or the invariant nucleotide 5' to the deletion site. A large number of potential targets for extension can be envisaged to affect the detection of the deletion and the wild type sequence, and which one is most appropriate will be dependant on such variables as the extend of the deletion, and the DNA sequence in and around the site of the deletion.

Figure 19:
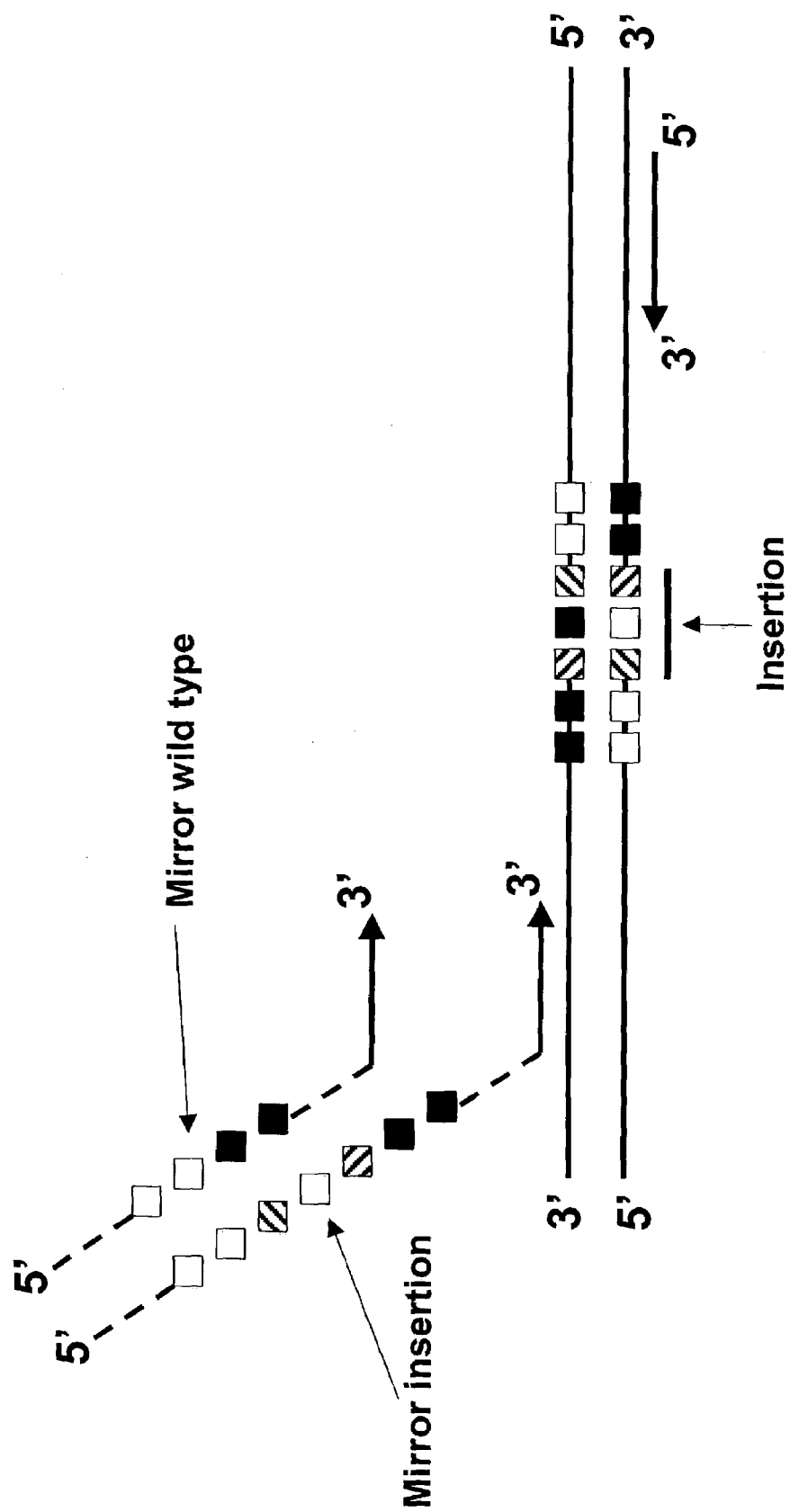
FIG. 19 illustrates how the system would amplify a target nucleotide in which the variant nucleotide arises as the result of an insertion.

FIG. 19 illustrates that the system can also be used to detect insertions, in a manner analogous to the detection of deletions. The amplification primer is shown to bear a 5' tag sequence which mimics the sequence of the insertion targeted, but it will be clear that by combining equal proportions of initial amplification primers, one bearing the insertion in the 5' tag and the other bearing the wild type sequence of the target DNA, a population of amplicons will be produced in which the insertion and the wild type sequence are equally represented. Interrogation of the variant nucleotide in the 5' tag sequence can be directed either at a nucleotide within the insertion, or at an invariant nucleotide 5' to the site of the insertion. A large number of systems can be envisaged to affect the detection of the insertion and the wild type sequence, and which one is most appropriate will be dependant on such variables as the extend of the insertion, and the DNA sequence in and around the site of the insertion.

Figure 20:
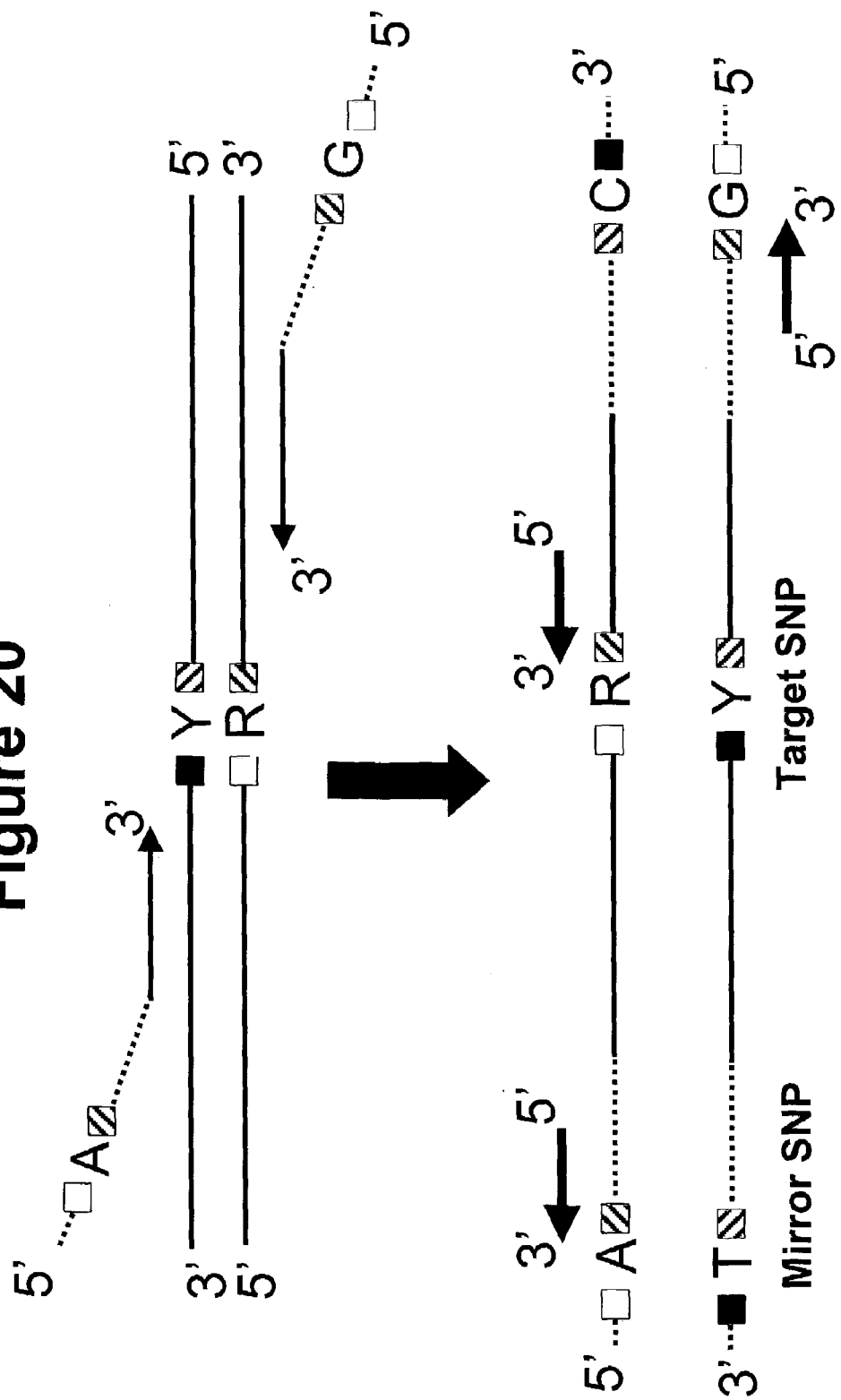
FIG. 20 illustrates the design of a system in which a variant nucleotide may be introduced through the use of two 5' tag primers, attached to two initial amplification primers.

FIG. 20 illustrates that a form of variant nucleotide may be introduced to the amplicon using two initial amplification primers each bearing an almost identical '5 tag tail, but differing in a variant nucleotide, which may be a single nucleotide, or a number of nucleotides, such as a deletion or an insertion. This system will generate a population of amplicons in which the variable nucleotide is represented on opposite strands of the amplicon, but the variable nucleotide forms will be balanced at a ratio approaching absolute 1:1. This system overcomes the problem of having to balance two separate primers competing for the same target DNA specific hybridization site. However, as a result of the extreme degree of homology between the 5' tag tails, it is possible that the initial amplification primers' 5' tails could bind to their own extension products 3' ends, either intermolecularly, or intra-molecularly. Careful design of assay conditions, and the thermal profile during the amplification in particular, is a necessity to ensure this does not interfere with the PCR amplification.

It will be appreciated by those of skill in the art, after having read and understood this disclosure, that a large plurality of embodiments employing the compositions and methods taught by this invention can be carried out without undue experimentation. Such embodiments include combinations of the embodiments disclosed herein. Further, one skilled in the art will appreciate that the introduction of exogenous sequences into amplicons by employing 5' tags comprising one or more variant nucleotides affords great versatility in designing identification primers. Further still, the employment of 5' tags in identification primers, such as for purposes of identification, capture, and/or detection, will similarly be appreciated by one skilled in the art as an advantage that affords great versatility for analysis of results. These and other advantages will become apparent to one skilled in the art upon reading and understanding this disclosure.

One skilled in the art will appreciate that through judicious choice of exogenous 5' sequences attached to identification primers, large multiplex amplifications can be constructed that can generate products capable of aiding both the interpretation of individual detection primer reactions, and in the overall interpretation of the multiplex assay, by utilizing the individual primers as control components in the assay.

In a preferred embodiment of the invention, analysis of the products of the primer extension reactions can be done so as to determine the relative abundance of labeled identification primers. Abundance analysis can be undertaken by comparing the identity of the nucleotide incorporated into an identification primer, the identity of the identification primer (that is, whether it is a probe of a 5' tag sequence or a naturally occurring polymorphism in the target nucleic acid), the signal strength of the identification primers, and then comparing the relative signal strengths of the primers to determine the relative success of each of the primer extension reactions that occurred (that is, the amplification and identification reactions). In this way, one skilled in the art can troubleshoot a primer extension reaction, or a combined amplification-primer extension reaction, by examining the relative abundance of the labeled primers and comparing the signals observed from known primers to the known ratios of variable nucleic acids induced by the 5' tag sequences into the amplicons. In this way, one skilled in the art can learn, in a single reaction run, whether problematic results arose due to sub-optimal amplification, sub-optimal extension of the variant nucleotide, or a host of reaction parameters once the disclosure of this invention is in hand. This embodiment of the invention may be employed to advantage in multiplexed and high-throughput protocols, greatly simplifying troubleshooting of these reactions.

Being able to define the efficiency of incorporation of each of the nucleotides at a polymorphic site has great utility in the field of diagnostic genotyping, where the certainty of the result is critical. For example, in the filed of agricultural genotyping, it has recently been shown that the ovine PrP gene is frequently present in multiple copy numbers which complicates the analysis of this gene. Having a balanced heterozygote signal generated as part of the amplicon required to analyze PrP enables the rapid assessment of any samples which might display this phenomenon. Also, in pharmacogenomic analysis of large numbers of polymorphisms in a single reaction, having a balanced heterozygote produced as part of the amplicon enables confirmation of the production of that specific amplicon to assayable levels within the multiplex, and further provides a heterozygote polymorphism which mimics the specific polymorphism targeted, and thereby enable comparisons to be made and surety of the result called for each of the polymorphisms in the multiplex. In the forensic context, where mixed template samples are possible, the system described enables the generation of a standard curve, or linear relationship, between the efficiency of incorporation of one nucleotide over the other, and enables the assessment of levels of each nucleotide which must have been present in the original template. Here, any of a great number of polymorphisms may be utilized, and their characteristics assessed such that they can be combined in large multiplex reactions.

Many other applications of the specialized primers and methods taught herein will become apparent to one of ordinary skill in the art with the teaching of this disclosure in hand, including paternity testing, pharmacogenomic analysis, and the like.

Having now generally described the invention, the invention may be more readily understood through reference to the following examples, which are provided by way of illustration and are not intended to limit the present invention unless specified

EXAMPLES

The current invention has facilitates the analysis of two different types of samples: namely single source template DNA samples of high importance (medical diagnostic samples, for example) and secondly in the analysis of samples which may contain template DNA from more than one individual, as may be encountered during forensic DNA analyses.

Example 1

When analyzing DNA from a single source, it is possible to introduce artificial representations of the polymorphisms under investigation on the same amplicons as the targeted polymorphisms, such that the artificial representations are present at exactly the same concentration as the targeted polymorphisms. It is further possible to ensure that the sequence context of the true polymorphism is mimicked in the DNA flanking the artificial representation of the polymorphism. All other variables which may influence the efficiency of DNA polymerase-mediated nucleotide addition are automatically normalized between the real SNP and its artificial copy during a primer extension reaction simultaneously interrogating both real and artificial polymorphism. These variables are such things as salt concentration, pH, thermal profile, concentration of PCR components ($Mg^{++}$, buffer, additives such as BSA, dNTPs etc).

As an example, the SNP TSC0096009 has the following sequence:

```
5' flank: gttggctttc gtgtttgctg ctgtcctcat agatttcaca tggattagag gtcctccaaa tggagtgctg cccaccttga ccactctttc ccatgcttct tgcctgctgc ttcacatggt ccaggtggac tgcttttctc cccgcttaca tttcctagaa agtgccctgc tcaccctttt ctctggatgc tcactcaggg gttttaccag gcctgaactc tctcca SNP:      R(a/g)

3' flank: gctgtgccgc ttcacccaac tgaggccttc tcattcttca ctttgtagtc aaggaatctg   (SEQ. ID NO. 1)

cagcccagaa gctcctccat tttcctccag actagcccag gtctcatacc ctttggtttc accttctgt acttctttca tgttgcccag gataattcct catcattact tgtcaaatgg ttgtgttctc cctgggctac agattagatg aggttgggaa ttcccttttc actgcctctg tatctcaata gcagcccat gccaaacact tcccagggac tgagtaaaga tttccccaaa gggtgagtga atgttgagga aaggcagaaa gcaatcctcc ttaagtggga tatcagaatg ctgagcttaa cttgaaaccg tttctaaacc atagactctt atttaaagga aaccaacatg aaaatgccaa caccacctta tttacaaggt actttgttca ctagagctat taaagggctg tgttgatggg aagctgtgta taattgtagg tattatgcca gagaccgctt tctgtcaggc tgccagacca aaggggtagg gaccgtactc tagagaccct cacccaacag gatgattaaa cgaatttgta agggttaata gatgggcggt ggctcattaa aaccaactct aa
```

The polymorphic base is an R (G or A), which can be analyzed as either a G/A, or as a C/T on the complimentary strand. The region around this polymorphic site may be amplified in a standard PCR reaction using the following primers:

```
Forward (upper) Primer:              (SEQ. ID NO. 2)
   5'CCCTGCTCACCCTTTTCTCTGGATGCT3'

Reverse (lower) Primer:              (SEQ. ID NO. 3)
   5'GAGAAGGCCTCAGTTGGGTGAAGCG3'
```

These primers have annealing temperatures of Tm 71.6° C. and 70.1° C. respectively, and amplify a 97 bp PCR amplicon. A larger PCR amplicon is generated than this using the disclosed technology, where a 5' tag sequence unrelated to the target DNA modifies one of the primers such that it has a 'mirror' of the real targeted SNP. This 'mirror' is generated by replacing the forward primer (for example) with a 1:1 blend of the following two sequences:

```
Forward 'T' primer:                  (SEQ. ID NO. 4)
 5'TCCTCGATTAC*TTGTCAGCCCTGCTCACCCTTTTCTCTGGATGCT3'

Forward 'C' primer:                  (SEQ.ID NO. 5)
 5'TCCTCGATTAC*CTGTCAGCCCTGCTCACCCTTTTCTCTGGATGCT3'
```

The 5' tag sequence is shown underlined, with the position of the artificially generated SNP shown preceded by an asterisk. A small number of additional hybridizing bases may be included at the junction of the 5' tag sequence and the 5' end of the template specific sequence in order to counter the effects of the 5' tag sequence causing the local disruption of hybridization here (the G in the sequences above, for example, is a hybridizing base absent from the forward primer without the 5' tag sequence, SEQ ID 2). The reverse primer remains unaltered from that shown above (SEQ ID 3). Note that the product generated upon amplification using these primers and the common reverse will have two polymorphic sites represented: the original real SNP targeted, and mirror of this SNP in the DNA derived from the 5' tag sequences. Both sites have identical flanking bases (two bases to the 3' on the strand to be interrogated, and one base 5' to the interrogated site). Both these SNPs can now be interrogated using the following two primers, which will incorporate G/A bases:

Note that the terminal two bases at the 3' end of each of these primer sequences is CA (shown underlined), but that 5' of these two bases, there is imperfect homology such that under specific stringent conditions the two primers will not cross hybridize. The sequences are also different lengths, such that under analysis of the extension products on a fluorescent capillary electrophoresis instrument the results appear as two distinct but closely associated peaks (from the mirror SNP heterozygote) and an associated single or doublet peak which derives from the real SNP (see for example FIG. 4).

The ratio of incorporation of each of the terminating bases is maintained between the mirror SNP heterozygote and the real SNP heterozygote, allowing for accurate genotyping of the real SNP.

Example 2

In forensic applications, it may be required to analyze template DNA which originates from more than one individual. In these circumstances, it is beneficial to assume that every forensic template is a potential mixture, and to routinely analyze the DNA in such a manner as to enable the identification of a mixture, and the subsequent interpretation of the mixture is facilitated. Using transversion polymorphisms flanked by complimentary bases enables these requirements to be met.

Amplification of the SNP TSC0018292 will be used as an example of the analysis of a G/C SNP flanked by an A and a T. This will limit the sequence context 'mirror' of the

```
Real SNP probe (forward):    5'GGTTTTACCAGGCCTGAACTCTCTCCA3'   (SEQ ID NO. 6)
(Tm 68.1° C.)

Mirror SNP probe (reverse):  5'AGAAAAGGGTGAGCAGGGCTGACA3'     (SEQ ID NO. 7)
(Tm 67.0° C.)
``` analyzed polymorphism to one base 5' and one base 3'. The sequence of this SNP is:

```
5' flank: ctgccaagtg tagagtcgtc agggagcagg ccaggctggg ggctccctct gccctgacc
          cctgggggag ctgctgggag agtcctggcc tctcctgcat gtgcgtggct tgcttttgg
          ctggactaag gattgcagcc atatgaaatg ctcattgctg tcctcatccc cctcccattg
          gctgtcctgg aa
SNP:      S(c/g)
3' flank: tcagctcctt tctgcagggc agccactgca cacctttctt ctgtgtcctt tcaggatgtc  (SEQ. ID NO. 8)
          ctgtgcacac acaagtatat atatatacac atatgtgtac acacacatat ataaatccta
          ggattagaat ctctggctca agggattttg tgtcctgtag atactgtgtt ttcgttttc
```

```
                          -continued
    tgactttttc ctgcacactg tagactacac cgtgtgctac cctgcatttg cgattatcag ggaacatgtc ttggacgtcg tccacagcag ccccteccaga cctgcccatt cctcctgctc aggcattcca tactgtgaat cacttgctta accacacctt gactgatggg gacacttact tcttttcact gtgtcttata atgcagccct ggatatcctt acacttattt ccttggctac ttgtatgagg acctttgtag gattaaattt gataactaga attgtggatc aaaaggtttg tgcattttca ctttgataag gatgaccaca ccctaggatg gttggctggg atccctttct ctaacat
```

The S (G or C) polymorphism can be amplified using the following primer sequences:

```
Forward (upper) Primer:                 (SEQ. ID NO. 9)
    5'CCATATGAAATGCTCATTGCTGTCCTCA3'
Reverse (lower) Primer:                 (SEQ. ID NO. 10)
    5'GACACAGAAGAAAGGTGTGCAGTGGCTG3'
```

These primers have annealing temperatures of 68.3° C. and 70.1° C. respectively, and amplify a 102 bp amplicon. A significantly larger amplicon will be generated if these primers have 5' tag sequences added which will enable the artificial recreation of the targeted SNP at known concentrations. Suitable primers to enable this analysis are shown below:

```
5' tag Forward (upper) Primers:
5'CCAAAGATCCTCTGGAGCTAACTCCTATGGTCTA*GTTGCCATATGAAATGCTCATTGCTGTCCTCA3'    (SEQ. ID NO. 11)

and

5'CCAAAGATCCTCTGGAGCTAACTCCTATGGTCTA*CTTGCCATATGAAATGCTCATTGCTGTCCTCA3'    (SEQ. ID NO. 12)

5' tag Reverse (lower) Primers:
5'AAATCGGTTGGATTCGCTTGACGGAAGTATTGAGA*GTCGTGGACACAGAAGAAAGGTGTGCAGTGGCTG3' (SEQ. ID NO. 13)

and

5'AAATCGGTTGGATTCGCTTGACGGAAGTATTGAGA*CTCGTGGACACAGAAGAAAGGTGTGCAGTGGCTG3' (SEQ. ID NO. 14)
```

An asterisk precedes the base in the 5' tag tails which result in the generation of a controlled variant bases in the amplicon population. When the forward (upper strand) primers are used at a skewed ration of, for example, 3× the G bearing primer to 1× the C bearing primer, this generates a mirror SNP in which there is a 3× higher representation of the G base than the C base. This is reversed on the daughter strand such that there is a 3× higher representation of the C base over the G base. The reverse (lower strand) primers must be combined in the amplification reaction to be at equivalent concentrations of the G and C bearing sequences. This results in a mirror SNP which is a balanced heterozygote regardless of which strand is analyzed.

```
Skewed 3:1 Mirror SNP Forward Probe (upper):     5'(Tn)AGATCCTCTGGAGCTAACTCCTATGGTCTA3'    (SEQ. ID NO. 15)
(Tm 65.3° C.)

Skewed 1:3 Mirror SNP Reverse Probe (lower):     5'(Tn)ACAGCAATGAGCATTTCATATGGCAA3'        (SEQ. ID NO. 16)
(Tm 65.8° C.)

Balanced Het Mirror SNP Forward Probe (upper):   5'(Tn)GCACACCTTTCTTCTGTGTCCACGA3'         (SEQ. ID NO. 17)
(Tm 66.1° C.)

Balanced Het Mirror SNP Reverse Probe (lower):   5'(Tn)GGATTCGCTTGACGGAAGTATTGAGA3'        (SEQ. ID NO. 18)
(Tm 65.9° C.)
```

Note that each of these primers terminates in an A at the 3' end (shown underscored) and that each of the probes will extend to incorporate either a G or a C. The subsequent base in the amplicon template is then a T, and this sequence context is maintained regardless of strand. Further note that each probe is modified to include a number of non-hybridizing bases (for example, a number of Ts, here represented by ($T_n$)). These additional bases are included to provide a means of altering the apparent migration of each extended probe to occupy a unique and predictable position on electrophoresis.

In addition to these probes which are designed to interrogate to the artificial mirror SNPs, the following two probes are used to interrogate the real SNP, which is the target of the initial amplification:

```
Forward (upper) Probe:              (SEQ. ID NO. 19)
     5'(T_n)CCTCCCATTGGCTGTCCTGGAA3'

Reverse (lower) Probe:              (SEQ. ID NO. 20)
     5'(T_n)GCTGCCCTGCAGAAAGGAGCTGA3'
```

In common with the probes interrogating the artificial SNPs, these probes have an A at their 3' terminus, ensuring sequence dependant effects are normalized. When these probes extend, they will incorporate either G or C or both G and C dependant on whether the original template DNA was homozygous (for G or C) or heterozygous (for G and C). The subsequent base in the template is again a T. If the original sample was a mixture of more than two individuals, it will be possible to identify this given that the combination of the two templates is not homozygous for either G or C, and that if heterozygous, combined templates do not represent an apparent balanced heterozygote, as might be generated by the combination of two (or more) individual templates which are opposite homozygotes in equivalent proportions, or the combination of two (or more) individual templates which are heterozygotes (and regardless of relative proportions).

Again, each of the primer extension probes listed above is modified to include a number of T bases at their 5' end, in order to separate these extension products to a unique area of the electrophoretogram.

The system described above will generate output similar to that shown in FIG. 13, which shows 6 SNPs concomitantly analyzed with only four extension primers per SNP system. This trace, and the mathematical manipulation of the data contained therein, allows the relationship between absolute ratio and observed ratio of areas (areas under each peak) to be determined, and the observed ratio of areas from the real SNP to be related back to an absolute ratio. For clarity, only one of each of the potential 1:1 mirror SNP extensions and one of the real SNP extensions is shown in FIG. 13.

In order to make the association between observed ratio of areas and absolute ratio of bases present at a certain polymorphic site, it is necessary to define the mathematical relationship between the absolute ratio and the observed ratio. This can be done for the TSC0018292 SNP by using the previously listed 5' tag primers (SEQ IDs 11 and 12) at a much wider range of ratios of G bearing primer to C bearing primer, but maintaining the other primers (SEQ IDs 13 and 14) at 1:1 ratio to provide a control from amplification tube to amplification tube. From the amplified DNA, only the mirror SNPs need be interrogated, to build a mathematical relationship between the absolute ratios and the observed ratios of areas. Indeed an artificial system may be developed to generate all possible SNPs with all possible local sequence contexts, without the need to amplify a variant DNA region, as only the artificially generated SNPs are required to be interrogated.

Example 3

A specific example of how this technology can be used is in the analysis of four SNP sites within a portion of the PrP gene from the sheep (*Ovis aries*). This example has aspects of both the amplification of a single source template, and the interpretation of a mixed template, as the ovine PrP gene may be present in greater than two copies per cell in some animals, resulting in imbalanced (and apparently 'mixed') profiles being generated. This description may be better understood with reference to FIG. 16.

The initial amplification is undertaken using the following primer sequences:

```
5' tag Forward (upper) Primers:
5'TGAGGATCCACTGGATAGCTGAAGCTCTGGACA*CGATG*ACATCGTCAAGGTGGTAGCCACAGTCAGTGGAACAAG3'    (SEQ. ID NO. 21)

and

5'TGAGGATCCACTGGATAGCTGAAGCTCTGGACA*TGATG*GCATCGTCAAGGTGGTAGCCACAGTCAGTGGAACAAG3'    (SEQ. ID NO. 22)

5' tag Reverse (lower) Primers:
5'ATGCACGCATAGCTGATACGGTCACCTGTA*ACATC*CGAAGGTGGTGGTGGTGACTGTGTGTTGCTTGAC3'           (SEQ. ID NO. 23)

and

5'ATGCACGCATAGCTGATACGGTCACCTGTA*CCATC*TGAAGGTGGTGGTGGTGACTGTGTGTTGCTTGAC3'           (SEQ. ID NO. 24)
```

As before, nucleotides directing the generation of a variant nucleotide in the amplicon population are preceded by an asterisk. Note that there are two such positions in the 5' tag tails of each of the primers. Use of these primers in equivalent concentrations in the initial amplification will generate an amplicon of 390 bp, with the four targeted SNPs recreated in the terminal ends of the amplicons such that they can be interrogated to return a balanced heterozygote signal for each. These balanced heterozygotes may be generated by adding the following sequences to the primer extension reaction:

```
Mirror 136 Probe:    5'(Tn)TGACTGTGGCTACCACCTTGACGATG3'    (SEQ. ID NO. 25)

Mirror 154 Probe:    5'(Tn)TCCACTGGATAGCTGAAGCTCTGGACA3'   (SEQ. ID NO. 26)

Mirror 171-1 Probe:  5'(Tn)AACACACAGTCACCACCACCACCTTC3'    (SEQ. ID NO. 27)

Mirror 171-2 Probe:  5'(Tn)CACGCATAGCTGATACGGTCACCTGTA3'   (SEQ. ID NO. 28)
```

These probes are modified at their 5' end to include non-hybridizing bases, which are represented by $(T_n)$. These sequences do not contribute to the binding of the probe to the target sequence within the amplicon, but merely modify the position that the extended probes will migrate to under electrophoresis, ensuring that the real SNP probes and the mirror SNP probes will migrate with distinct properties. An image of the output from this system is presented as FIG. 17, where the real SNPs are all shown as the heterozygote form, whereas in reality this is unlikely to ever occur for this particular ovine system. However, the mirror SNPs are accurately shown to return a balanced heterozygote signal for each SNP. The ratio between the area of each peak in the heterozygote mirror acts as a confirmation of the heterozygosity of the corresponding real SNP.

It might be expected that an imbalanced profile would deviate significantly from the normal heterozygote area ratios defined by the mirror SNPs, and such an imbalanced profile may be indicative of additional genetic material being present in the template used to seed the amplification reaction. It is possible to assess the area ratios at the mirror SNPs and use these ratios to automatically assess the balance observed at the appropriate real SNPs, and pass or fail a profile as being normal or imbalanced. This functionality is additional to the ability to automatically genotype SNPs using this primer extension technology.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of performing a primer extension reaction, comprising:
   obtaining an amplicon having a sequence generated from a target nucleic acid and a sequence generated from a first strand amplification primer, by amplifying a target nucleic acid having a nucleotide sequence containing a variant nucleotide flanked by an invariant nucleotide, wherein a first strand amplification primer is employed that comprises a 5' tag substantially incapable of hybridizing to the target nucleic acid under amplification conditions, and wherein the 5' tag contains the same nucleotide bases in sequence as the variant nucleotide and the invariant nucleotide of the target nucleic acid, and employing a second strand amplification primer;
   employing the amplicon in a primer extension reaction wherein the identity of the variant nucleotide in the sequence generated from the target nucleic acid is determined by hybridizing a first identification primer immediately adjacent to the variant nucleotide in the sequence generated from the target nucleic acid;
   hybridizing a second identification primer immediately adjacent to the variant nucleotide in the sequence generated from the 5' tag of the first strand amplification primer;
   extending the first and the second identification primers in the presence of one or more nucleotides and a polymerizing agent;
   determining the identity of the variant nucleotide generated from the target nucleic acid; and
   comparing extension product of the first identification primer and extension product of the second identification primer, thereby performing the primer extension reaction.

2. A method according to claim 1, wherein immediately adjacent in the 5' direction to the variant nucleotide in the 5' tag is the invariant nucleotide to the 5' direction of the variant nucleotide of the target nucleic acid.

3. A method according to claim 1, wherein immediately adjacent in the 3' direction to the variant nucleotide in the 5' tag is the invariant nucleotide to the 3' direction of the variant nucleotide of the target nucleic acid.

4. A method according to claim 1, wherein immediately adjacent in the 3' direction to the variant nucleotide in the 5' tag is the invariant nucleotide to the 3' direction of the variant nucleotide of the target nucleic acid, and immediately adjacent in the 5' direction to the variant nucleotide in the 5' tag is the invariant nucleotide to the 5' direction of the variant nucleotide of the target nucleic acid.

5. A method according to claim 1, wherein the 5' tag has at least two invariant nucleotides immediately adjacent in the 3' direction to the variant nucleotide, and at least two invariant nucleotides immediately adjacent in the 5' direction to the variant nucleotide, and wherein the at least two invariant nucleotides immediately adjacent in the 3' direction and the at least two invariant nucleotides immediately adjacent in the 5' direction are selected so as to be homologous to the nucleotides flanking the variant nucleotide in the target nucleic acid.

6. A method according to claim 1, wherein the first and the second identification primers bear a detectable characteristic.

7. A method according to claim 6, wherein the detectable characteristic on the first identification primer is different from the detectable characteristic on the second identification primer.

8. A method according to claim 1, wherein the identity of the variant nucleotide in the 5' tag is varied so as to generate a population of amplicons in which the identity of the variant nucleotide is fixed at a known ratio.

9. A method according to claim 8, wherein the identity of the variant nucleotide in the 5' tag is varied so as to generate a population of amplicons that is a balanced heterozygous population with respect to the variant nucleotide.

10. A method according to claim 1, wherein the target nucleic acid comprises nucleic acids from two or more individuals.

11. A method according to claim 1, wherein two or more variant nucleotides are identified.

12. A method according to claim 11, wherein the two or more variant nucleotides are on the same nucleic acid molecule.

13. A method according to claim 11, wherein the two or more variant nucleotides are on different nucleic acid molecules.

14. A method according to claim 1, wherein the identification primers are extended by one or more labeled nucleotide bases, and are capable of being detected by a characteristic selected from the group consisting of mass, apparent mass, molecular weight, apparent molecular weight, a combination or ratio of mass and charge, number of bases, magnetic resonance, spectrophotometry, fluorometry, electric charge, polarimetry, light scattering, luminescence and antigen-antibody interaction.

15. A method according to claim 1, wherein the identification primers are extended by a chain terminator.

16. A method according to claim 14, wherein the chain terminator is a dideoxynucleotide or an acyclo terminator.

17. A method according to claim 14, wherein the chain terminator is labeled with a detectable moiety.

18. A method according to claim 14, wherein the identification primers comprise a tag capture moiety.

19. A method according to claim 18, wherein the identification primers are captured on an array.

20. A method according to claim 19, wherein the array is an addressable array.

21. A method according to claim 19, wherein the array is a virtual array.

22. A method of performing a primer extension reaction, comprising:
   obtaining a sample comprising target nucleic acid from one or more individuals;
   obtaining an amplicon population having a sequence generated from the sample and a sequence generated from a tagged first strand amplification primer, by amplifying nucleic acids in the sample having a nucleotide sequence containing a variant nucleotide that is a transversion flanked in the 5' direction by an invariant nucleotide and flanked in the 3' direction by an invariant nucleotide, wherein the tagged first strand primer employed comprises a 5' tag substantially incapable of hybridizing to target nucleic acids in the sample, and wherein the 5' tag contains the same nucleotide bases in sequence as the variant nucleotide and the 3' and 5' flanking invariant nucleotides of the target nucleic acid, and wherein a second strand amplification primer is employed;
   employing the amplicon population in a primer extension reaction wherein the identity of the variant nucleotide in the sequence generated from the sample is determined by hybridizing a first identification primer immediately adjacent to the variant nucleotide in the sequence generated from the sample;

hybridizing a second identification primer immediately adjacent to the variant nucleotide in the sequence generated from the amplification primer;

extending the first and the second identification primers in the presence of one or more nucleotides and a polymerizing agent;

determining the identity of the variant nucleotide generated from the sample; and comparing extension product of the first identification primer and extension product of the second identification primer, thereby performing the primer extension reaction.

23. A method according to claim 22, wherein the flanking invariant nucleotide in the 5' direction is complementary to the flanking invariant nucleotide in the 3' direction.

24. A method according to claim 22, wherein the first strand amplification primer comprises the two or more nucleotides in the 5' direction immediately adjacent to the variant nucleotide of the first strand amplification primer, wherein the two or more nucleotides are identical to the two or more nucleotides immediately adjacent in the 5' direction of the variant nucleotide in the target.

25. A method according to claim 22, wherein the first strand amplification primer comprises the two or more nucleotides in the 3' direction immediately adjacent to the variant nucleotide of the first strand amplification primer, wherein the two or more nucleotides are identical to the two or more nucleotides immediately adjacent in the 3' direction of the variant nucleotide in the target nucleic acid.

26. A method according to claim 22, wherein the first strand amplification primer comprises the two or more nucleotides in the 5' direction immediately adjacent to the variant nucleotide of the first strand amplification primer, and the two or more nucleotides in the 3' direction immediately adjacent to the variant nucleotide of the first strand amplification primer, each arranged as to be identical to the corresponding nucleotides flanking the variant nucleotide in the target nucleic acid.

27. A method according to claim 23, wherein the second strand amplification primer comprises a 5' tag having the variant nucleotide.

28. A method according to claim 27 wherein the variant nucleotide is flanked by the same complementary flanking invariant nucleotides in the target nucleic acid.

29. A method according to claim 28, wherein the identity of the variant nucleotide in the 5' tag is varied so as to generate a population of amplicons wherein the identity of the variant nucleotide is varied at a known ratio.

30. A method according to claim 28, wherein the identity of the variant nucleotide in the 5' tag of the first strand amplification primer and the second strand amplification primer is varied so as to generate an amplicon population comprising a ratio of 1:1 and a ratio of 3:1 with respect to the identity of the nucleotides in the amplicon population generated by the 5' tags.

31. A method according to claim 22, wherein the first and the second identification primers bear a detectable characteristic.

32. A method according to claim 22, wherein the detectable characteristic on the first identification primer is different from the detectable characteristic on the second identification primer.

33. A method according to claim 22, wherein two or more variant nucleotides are identified.

34. A method according to claim 33, wherein the two or more variant nucleotides are on the same nucleic acid molecule.

35. A method according to claim 33, wherein the two or more variant nucleotides are on different nucleic acid molecules.

36. A method according to claim 22, wherein the identification primers are extended by one or more labeled nucleotide bases, and are capable of being detected by a characteristic selected from the group consisting of mass, apparent mass, molecular weight, apparent molecular weight, a combination or ratio of mass and charge, number of bases, magnetic resonance, spectrophotometry, fluorometry, electric charge, polarimetry, light scattering, luminescence and antigen-antibody interaction.

37. A method according to claim 22, wherein the identification primers are extended by a chain terminator.

38. A method according to claim 37, wherein the chain terminator is a dideoxynucleotide or an acyclo terminator.

39. A method according to claim 37, wherein the chain terminator is labeled with a detectable moiety.

40. A method according to claim 22, wherein the identification primers comprise a tag capture moiety.

41. A method according to claim 40, wherein the identification primers are captured on an array.

42. A method according to claim 41, wherein the array is an addressable array.

43. A method according to claim 41, wherein the array is a virtual array.

44. A method according to claim 23, wherein the second strand amplification primer comprises a 5' tag having the same variant nucleotide, the same invariant nucleotide flanked in the 5' direction, and the same invariant nucleotide flanked in the 3' direction as the first strand amplification primer, and wherein the first strand amplification primer reflects a transversion ratio of 1:1 in the variant nucleotide and wherein the second strand amplification primer reflects a transversion ratio of 1:3 in the variant nucleotide, and wherein at least three identification primers are employed in the primer extension reaction.

45. A method of performing primer extension utilizing at least two amplification primers comprising:

obtaining a target nucleic acid comprising a nucleotide sequence having a variant nucleotide flanked by an invariant nucleotide;

hybridizing to the target nucleic acid a first amplification primer having a 5' tag comprising the same nucleotide bases in sequence as the variant nucleotide flanked by the invariant nucleotide of the target nucleic acid, wherein the 5' tag is substantially unable to hybridize to the target nucleic acid, and hybridizing a second amplification primer; and extending the amplification primers in the presence of at least one or more nucleotides and a polymerizing agent, thereby performing primer extension.

46. A method of performing a primer extension reaction, comprising:

obtaining a sample comprising target nucleic acid from one or more individuals;

obtaining an amplicon population having a sequence generated from the sample and a sequence generated from a tagged first strand amplification primer, by amplifying nucleic acids in the sample having a variant nucleotide, wherein the tagged first strand primer is employed that comprises a 5' tag substantially incapable of hybridizing to target nucleic acids in the sample, and wherein the 5' tag contains the same nucleotide base as the variant nucleotide of the sample, and wherein a second strand amplification primer is employed;

employing the amplicon population in a primer extension reaction wherein the identity of the variant nucleotide in the sequence generated from the sample is determined by hybridizing a first identification primer immediately adjacent to the variant nucleotide in the sequence generated from the sample;

hybridizing a second identification primer immediately adjacent to the variant nucleotide in the sequence generated from the amplification primer;

extending the first and the second identification primers in the presence of one or more nucleotides and a polymerizing agent;

determining the identity of the variant nucleotide generated from the sample; and comparing extension product of the first identification primer and extension product of the second identification primer, thereby performing the primer extension reaction.

47. A method according to claim 46, wherein the variant nucleotide represents a transversion.

48. A method according to claim 1, wherein the variant nucleotide of the target can be a wild-type nucleotide base or mutant nucleotide base, and at least two first strand amplification primers are employed, each first strand amplification primer having a 5' nucleic acid tag, the first 5' tag of the at least two first strand amplification primers comprises the same nucleotide base as the mutant nucleotide base and the second 5' tag of the at least two first strand amplification primers comprises the same nucleotide base as the wild-type nucleotide base, the first 5' tag and the second 5' tag being employed at a known ratio so that a population of amplicons is generated having the wild-type and mutant nucleotide base represented at a known ratio.

49. A method according to claim 48, wherein the first 5' tag and the second 5' tag differ from each other by one nucleotide base.

50. A method according to claim 49, wherein the one nucleotide base that the first and the second 5' tag differ is the same nucleotide base as the wild-type or the mutant nucleotide base.

* * * * *